US012558483B2

(12) United States Patent
Heiniger et al.

(10) Patent No.: US 12,558,483 B2
(45) Date of Patent: Feb. 24, 2026

(54) AUTOINJECTOR WITH MULTICHAMBER PRODUCT CONTAINER

(71) Applicant: Ypsomed AG, Burgdorf (CH)

(72) Inventors: Lukas Heiniger, Lotzwil (CH); Jürgen Wittmann, Burgdorf (CH); Peter Stettler, Ersigen (CH)

(73) Assignee: Ypsomed AG, Burgdorf (CH)

( * ) Notice: Subject to any disclaimer, the term of this patent is extended or adjusted under 35 U.S.C. 154(b) by 727 days.

(21) Appl. No.: 17/957,434

(22) Filed: Sep. 30, 2022

(65) Prior Publication Data

US 2023/0022361 A1      Jan. 26, 2023

Related U.S. Application Data

(63) Continuation of application No. PCT/EP2021/056310, filed on Mar. 12, 2021.

(30) Foreign Application Priority Data

Mar. 30, 2020      (CH) ...................................... 00379/20

(51) Int. Cl.
| | |
|---|---|
| *A61M 5/20* | (2006.01) |
| *A61M 5/315* | (2006.01) |
| *A61M 5/32* | (2006.01) |

(52) U.S. Cl.
CPC ...... *A61M 5/2033* (2013.01); *A61M 5/31596* (2013.01); *A61M 5/3204* (2013.01); *A61M 5/326* (2013.01); *A61M 2005/2013* (2013.01)

(58) Field of Classification Search
CPC .............. A61M 5/2066; A61M 5/2033; A61M 5/31596; A61M 5/3204; A61M 5/326; A61M 2005/2013
See application file for complete search history.

(56) References Cited

U.S. PATENT DOCUMENTS 4,394,863 A      7/1983  Bartner

FOREIGN PATENT DOCUMENTS

| | | | |
|---|---|---|---|
| CH | 714525 A2 | 6/2019 | |
| CH | 717267 A2 | 9/2021 | |
| EP | 2742962 A2 | 6/2014 | |
| WO | WO-9748430 A1 * | 12/1997 | .......... A61M 5/2033 |

(Continued)

OTHER PUBLICATIONS

International Search Report and Written Opinion issued for International Application No. PCT/EP2021/056310, issued on Jun. 21, 2021, 13 pages including 2 pages of English translation.

(Continued)

*Primary Examiner* — Edelmira Bosques
(74) *Attorney, Agent, or Firm* — Dorsey & Whitney LLP

(57)      ABSTRACT
An autoinjector for discharging one or more liquid products includes: a housing containing a multichamber product container, which includes a syringe body and an injection needle rigidly arranged at the distal end of the syringe body. The syringe body includes a first chamber for a first liquid product, a second chamber for a second liquid product, and a bypass for fluidically connecting the first chamber and second chamber. The bypass is formed in or on the syringe body in the form of a curved section protruding radially outwards, and two plungers are arranged in the syringe body in an axially movable manner.

6 Claims, 9 Drawing Sheets

(56) References Cited

FOREIGN PATENT DOCUMENTS

| WO | WO-2007131013 A1 | * | 11/2007 | .......... A61M 5/2066 |
|----|------------------|---|---------|------------------------|
| WO | 2017055462 A1 | | 4/2017 | |
| WO | 2018018167 A1 | | 2/2018 | |
| WO | 2019197493 A1 | | 10/2019 | |
| WO | 2020136124 A1 | | 7/2020 | |
| WO | 2021197804 A1 | | 10/2021 | |

OTHER PUBLICATIONS

International Preliminary Report on Patentability issued in International Application No. PCT/EP2021/056310, mailed on Sep. 29, 2022, 8 pages.
Third Party Observation filed in International Application No. PCT/EP2021/056310 on Jul. 29, 2022, 1 page.

* cited by examiner

AUTOINJECTOR WITH MULTICHAMBER PRODUCT CONTAINER

CROSS-REFERENCE TO RELATED APPLICATIONS

This application claims priority to International Patent Application No. PCT/EP2021/056310, filed Mar. 12, 2021, entitled "AUTOINJECTOR WITH MULTICHAMBER PRODUCT CONTAINER," which in turn claims priority to Swiss Patent Application No. CH 00379/20, filed Mar. 30, 2020, entitled "AUTOINJECTOR WITH MULTICHAMBER PRODUCT CONTAINER", each of which is incorporated by reference herein, in their entirety and for all purposes.

TECHNICAL FIELD

Disclosed are autoinjectors, also referred to as automatic injection devices, for automatically discharging a product or a plurality of products contained in a multichamber product container after triggering. The product or the plurality of products may be a liquid product or plurality of liquid products, and may be at least one medication or different medications.

BACKGROUND

The term "medication" here comprises any flowable medical formulation which is suitable for controlled administration through a means such as a cannula or hollow needle, for example comprising a liquid, a solution, a gel, or a fine suspension which contains one or more medical active ingredients. A medication can be a single active ingredient composition or a pre-mixed or co-formulated composition having a plurality of active ingredients from a single container. Medication comprises drugs such as peptides (e.g., insulins, insulin-containing medications, GLP-1-containing and derived or analogous preparations), proteins and hormones, biologically obtained or active ingredients, active ingredients based on hormones or genes, nutrient formulations, enzymes and further substances both in solid (suspended) or liquid form but also polysaccharides, vaccines, DNS or RNS or oligonucleotides, antibodies or parts of antibodies, and suitable base, auxiliary and excipient substances.

Multichamber product containers are known in the prior art. WO2017/055462 A1 discloses multichamber syringes which each have a bypass, a first and a second chamber, where the first and the second chamber each comprise a liquid product. In these multichamber syringes, the liquid product to be administered can be mixed shortly before application, or the liquid products can be sequentially administered, e.g., as a first and a second liquid product. Whether a mixed liquid product is administered from a multichamber syringe or a plurality of liquid products is sequentially administered from a multichamber syringe depends on the axial arrangement of the bypass in or on the multichamber syringe.

Furthermore, autoinjectors are known in the prior art. From EP2742962 A2, an injection device is known which automatically discharges a product after triggering after an axial displacement of a needle shielding sleeve in the proximal direction.

SUMMARY

It is an object of the present disclosure to provide a robust autoinjector, which automatically discharges the product to be administered, where the product to be administered is mixed only shortly before administration, or where a plurality of products is administered sequentially.

The object is achieved according by the autoinjector of the disclosed implementations.

The autoinjectors according to the present disclosure include a housing and a multichamber product container arranged in the housing. The multichamber product container may be a multichamber syringe, which may include a syringe body, an injection needle being rigidly arranged at the distal end of said syringe body. The syringe body may include a tapering portion or region at the distal end, where a needle holding portion may be provided at the distal end of the tapering portion or region. An injection needle may be rigidly arranged on the needle holding portion. The injection needle may project from the needle holding portion of the multichamber syringe in the distal direction. The cylindrical syringe body may include one or, alternatively, a plurality of bypasses, a first chamber for a first product, such as a first liquid product and a second chamber for a second product such as a second liquid product, where in the initial position, the two liquid products are separated from one another by a plunger. The separate storage of the two liquid products can, for example, increase the shelf life of the medication, because the mixed liquid product may only have a relatively short storage life or of none. Furthermore, the therapy of a disease may require a combined administration of medications, e.g., administration of a mixed liquid product at a time, or a sequential administration of medications, e.g., administration of different liquid products in succession, where separate storage of the two liquid products in a multichamber syringe may be necessary. The bypass may be formed in or on the syringe body as a curved section projecting radially outward. The bypass may serve to fluidically connect the first and second chambers. The bypass may be formed in or on the syringe body in such a way that a liquid product can flow from the first chamber into the second chamber. Two plungers may be arranged in the syringe body so as to be axially movable. The two plungers may sealingly rest against the inner diameter of the hollow cylindrical syringe body and may be moved axially along the syringe body. The first chamber of the syringe body may be arranged between the first and the second plunger. The second chamber of the syringe body may be provided between the second plunger and the distal end of the syringe body. The first plunger may be arranged proximally to the second plunger in the syringe body. The bypass may be formed axially longer than the second plunger. The axial length of the bypass and the axial length of the second plunger may be adapted such that the liquid product, provided in the first chamber, can flow through the bypass when the second plunger is arranged in the region of the bypass. The first or the first and second plunger can be moved axially in the distal direction within the syringe body such that the liquid product, such as the medication arranged in the first and second chambers, is discharged by the multichamber syringe through the injection needle.

If a mixed liquid product is to be administered to a patient, a pressure acting in the distal direction may be applied to the first plunger and may be transferred to the second plunger via the liquid product in the first chamber. When the first plunger is moved in the distal direction, the second plunger may thus also be moved, namely up to the region of the bypass. As a result of the bulge of the bypass, the liquid product can, if the second plunger is located completely in the region of the bypass, flow out of the first chamber past the second plunger into the second chamber and mix with the product located in the second chamber. The liquid product from the first chamber may be completely removed from the first chamber when the first plunger hits against the second plunger. The mixed product may then be discharged via the injection needle provided at the distal end of the syringe body by moving the two plungers in the distal direction along the hollow cylindrical housing portion up to the distal end of the syringe.

If the two products are to be administered sequentially to a patient, a pressure acting in the distal direction may be applied to the first plunger and is transferred to the second plunger via the liquid product provided in the first chamber. When the first plunger is moved in the distal direction, the second plunger is thus also moved. The displacement of the second plunger in the distal direction discharges the product provided in the second chamber through the injection needle arranged at the distal end of the syringe body. When the second plunger enters the region of the bypass, the product in the first chamber can flow into the second chamber via the bypass and mix with the liquid product that is or may be located in the second chamber and then be discharged through the injection needle arranged at the distal end of the syringe body. If no residual liquid, or only a little, is provided in the second chamber when the liquid product flows from the first chamber into the second chamber via the bypass, then a sequential administration of the liquid products is achieved. When the first plunger comes into contact with the second plunger, the liquid product provided in the first chamber may be completely or almost completely discharged.

Whether a mixed liquid product is to be discharged from a multichamber syringe or the two liquid products are to be discharged sequentially from a multichamber syringe through an injection needle arranged on the multichamber syringe, may depend on the axial position of the bypass on or in the syringe body. The more distally the bypass is arranged on or in the syringe body, or the closer the bypass is arranged on the injection needle provided at the distal end of the syringe body, the more likely the liquid product provided in the second chamber is administered first to a patient and thereafter the liquid product provided in the first chamber.

The housing may be elongated and defines the longitudinal axis of the autoinjector. The housing may be sleeve-shaped and/or cylindrical such as circular cylindrical. The multichamber syringe may be arranged in the housing. In embodiments, the multichamber syringe may be movably arranged in the housing, e.g., can be moved in the distal direction relative to the housing for an automatic piercing such that the needle tip of the injection needle protrudes from an opening at the distal end of the autoinjector and can be automatically inserted into the patient. With such a device, the needle tip of the injection needle may optionally be moved into the distal end of the device after the product has been discharged; and the multichamber syringe can be moved in the proximal direction relative to the housing.

In embodiments, the multichamber syringe may be accommodated along the longitudinal axis so as to be non-movable such as non-movable and/or rotationally fixed in the housing by means of a multichamber syringe holder, which may hold the multichamber syringe in an axially fixed manner such as in an axially and rotationally fixed manner, and may be connected such as by a snap-fit connection in an axially fixed manner, such as in an axially and rotationally fixed manner to the housing. The multichamber syringe may be accommodated in a multichamber syringe holder in an axially fixed manner such as in an axially and rotationally fixed manner. The multichamber syringe holder may be arranged in the housing in an axially fixed manner, such as in an axially and rotationally fixed manner.

The needle tip of the injection needle may project in the distal direction beyond the distal end of the housing. As a result, the injection needle may be inserted into the puncture site by means of a movement of the housing toward the patient. A needle shielding sleeve may be provided, which may form the distal end of the autoinjector and may have an opening for the injection needle, where the injection needle can pass through the opening. In its initial position, the needle shielding sleeve may be arranged in relation to the needle tip of the injection needle such that the needle shielding sleeve is distally beyond the needle tip of the injection needle, or such that the needle tip of the injection needle is distally beyond the distal end of the needle shielding sleeve. The needle shielding sleeve may be movable relative to the housing from its initial position in the proximal direction by an actuating stroke into an actuated position; it can be moved into the housing, so that the injection needle protrudes from the distal end or through the opening of the needle shielding sleeve or protrudes further. The needle shielding sleeve may be moved by a needle shielding stroke from the actuated position relative to the housing in the distal direction into a needle shielding position in which the distal end of the needle shielding sleeve is distally beyond the needle tip in order to prevent a risk of injury (e.g., needle stick) that would originate from an exposed needle tip of the injection needle after the device is used or after the discharge of the product has been completed. The needle shielding sleeve may, for example, be moved against the force of a spring, which may be referred to as needle shielding spring, in the proximal direction, where the spring, which is, for example, the second spring described herein or a spring separate therefrom, can move the needle shielding sleeve from the actuated position in the distal direction, e.g., into the needle shielding position. The autoinjector may have a locking member, which, for example, may be resiliently arranged and locks the needle shielding sleeve in its needle shielding position with respect to the housing, and blocks a pushing back of the needle shielding sleeve in the proximal direction or into the housing. The locking member locks the needle shielding sleeve at least such that the injection needle cannot protrude from the distal end of the needle shielding sleeve. The needle shielding sleeve can, for example, be moved from the needle shielding position only to such an extent in the proximal direction that the needle tip does not protrude from the distal end of the needle shielding sleeve.

The multichamber syringe holder may be connected in an axially fixed manner, such as in an axially and rotationally fixed manner to the housing. The multichamber syringe holder may be frictionally and/or positively connected to the housing, for example by a snap-fit.

In embodiments, the multichamber syringe holder may be pre-snap-fit with the housing and may be moved axially relative to the housing in the distal direction after insertion of the multichamber syringe in such a way that the multichamber syringe holder snap-fits into the housing. In the initial position, the multichamber syringe holder may be snap-fit to the housing. For this purpose, a cam/recess connection between the multichamber syringe holder and the housing can be provided. In a preassembled position, the multichamber syringe holder may be pre-snap-fit to the housing, where a multichamber syringe can be inserted into the autoinjector. For this purpose, a further cam/recess connection between the multichamber syringe holder and the housing can be provided. The multichamber syringe holder may include a cam, which can latch into a first recess provided on the housing and into a second recess provided on the housing. The first recess of the housing may be arranged proximally to the second recess of the housing. In the pre-mounted position, the cam of the multichamber syringe holder may be snapped into the first recess of the housing.

Alternatively, in the pre-mounted position, the cam of the multichamber syringe holder may be in stop contact with the first recess of the housing in the distal direction, and a stop contact may be provided between the needle shielding sleeve and the multichamber syringe holder in the proximal direction. In the initial position, the cam of the multichamber syringe holder may be snapped into the second recess of the housing. Alternatively, the multichamber syringe holder may have a recess and the housing that includes a first and a second cam in order to realize the snap-fitting between the multichamber syringe holder and the housing.

In alternative embodiments, the multichamber syringe holder may be snap-fit to the housing without pre-snap-fitting. For this purpose, a cam/recess connection between the multichamber syringe holder and the housing may be provided. In alternative embodiments, other connections may be provided between the multichamber syringe holder and the housing in order to form an axially fixed connection or an axially and rotationally fixed connection.

In further alternative embodiments, the multichamber syringe holder and the housing may be formed in one piece. Alternatively, the housing may be configured in such a way that a multichamber syringe can be held in an axially fixed manner, such as in an axially and rotationally fixed manner.

The multichamber syringe holder, or alternatively the housing, may include a cutout for the bypass of the multichamber syringe. The cutout may serve for axially fixing, such as an axially and rotationally fixed accommodation of the bypass of the multichamber syringe. The cutout may be configured such that the bypass can be accommodated therein or thereon. The cutout may be provided in a hollow cylindrical syringe holder body or housing body. The cutout may be formed continuously or with separations. The cutout may extend in the longitudinal direction. In embodiments, the cutout of the multichamber syringe holder may include a distal stop and a proximal stop. The multichamber syringe may be arranged in an axially fixed manner between the distal and the proximal stop when the multichamber syringe is inserted in the multichamber syringe holder or housing. The cutout and/or the proximal stop and/or the distal and the proximal stop may be configured to be elastically and/or plastically deformable. It may also be provided that only the proximal stop is configured to be elastically and/or plastically deformable. In alternative embodiments, the cutout may have only a distal stop. When the multichamber syringe is inserted in the multichamber syringe holder, a force acting on the multichamber syringe in the distal direction may hold the multichamber syringe against the distal stop. The multichamber syringe may be held in an axially fixed manner in the multichamber syringe holder, or elastically resiliently in the multichamber syringe holder.

In embodiments, the cutout of the multichamber syringe holder may be configured such that the multichamber syringe and the multichamber syringe holder or the housing are arranged rotationally fixed relative to each other. The cutout of the multichamber syringe holder and/or of the housing can be tapered, for instance tapered in the distal direction. The tapering in the multichamber syringe holder or housing may serve as an anti-rotation lock between the multichamber syringe and the multichamber syringe holder or housing. The tapering in the multichamber syringe holder or housing may be configured to be elastic and/or plastically deformable.

In alternative embodiments, only the distal stop of the cutout of the multichamber syringe holder or of the housing may be configured to taper in order to form an anti-rotation lock between the multichamber syringe and the multichamber syringe holder or housing.

The multichamber syringe may include an injection needle, which may be non-detachably fastened to the needle holding portion of the syringe body. A needle shielding cap, such as a soft needle shield (SNS) or rigid needle shield (RNS) known from the prior art, may be fastened, detachably fastened, to the needle holding portion. The needle shielding cap may, for example, be fastened to the holding portion in a friction-locking or positive-locking manner or in a combined friction-locking and positive-locking manner. The needle shielding cap may surround the injection needle and seal it in a sterile manner with respect to the environment. A soft needle shield (SNS) may include or consist of an elastomer, for example, a part formed on a rubber or caoutchouc basis (e.g., natural rubber including polymers of isoprene), which surrounds the needle. The soft needle shield (SNS) may include a soft surface made of, e.g., a rubber-like or caoutchouc-like material on its outer circumference. A rigid needle shield (RNS) usually has a plurality of parts, such as an elastomeric cap-shaped inner part and a sleeve-shaped or cap-shaped outer part made of a solid, e.g., non-elastomeric, plastic, which may receive the elastomeric part and is thus may be connected in a substantially non-detachable manner. The outer sleeve-shaped or cap-shaped part may surround the inner cap-shaped part and may, for example, be non-detachably connected to the inner cap, so that the outer and inner cap form a unit. The inner part may be formed from a harder plastic than the inner part. The outer part may be, for example, polyethylene, polystyrene, polypropylene or another suitable plastic. The inner part may be formed, for example, from rubber or caoutchouc or another suitable material.

The needle shielding cap, which covers the injection needle and on which a needle holding portion extending conically in the direction of the needle tip is fastened, may keep the injection needle protected from dirt and sterile. A gap may be formed between the tapering portion and the needle shielding cap (e.g., the sleeve made of hard plastic).

The multichamber syringe holder can may include at least one engagement member such as a shoulder against which the tapering portion of the multichamber syringe braces in the distal direction and which engages in the gap between the needle shielding cap and the tapering portion. Advantageously, the tapering portion resting against the engagement member may prevent the multichamber syringe from moving in the distal direction relative to the multichamber syringe holder.

A gap may be formed or may exist between the engagement member of the multichamber syringe holder and the needle shielding cap of the multichamber syringe, so that the needle shielding cap remains unloaded by the engagement member. This may prevent the sterility of the injection needle from being impaired by an unintentional displacement of the needle shielding cap by the engagement member.

In embodiments, the syringe body may include at its proximal end a flange, which may also be referred to as a finger flange, where a gap is formed between the flange and the syringe body when the tapering portion rests against the engagement member of the multichamber syringe holder, where the flange remains substantially unloaded. This may prevent the flange from being overloaded and the syringe body breaking.

The housing of the autoinjector may, for example, have a first holding portion, which may rest against the multichamber syringe holder such as on an outer surface or an outer circumference of the multichamber syringe holder and may prevent the at least one engagement member of the syringe holder from moving away from the longitudinal axis transversely to the longitudinal axis. The first holding portion may be cylindrical and may surround the at least one engagement member, or two or three or four engagement members, so that the at least one engagement member is arranged within the first holding portion. For the installation or insertion of the multichamber syringe into the multichamber syringe holder, the multichamber syringe holder may be located outside the region of the first holding portion of the housing. The holding region of the housing may be axially offset in the distal direction from the engagement member of the multichamber syringe holder. When the multichamber syringe is completely inserted into the multichamber syringe holder, the at least one engagement member engages in the gap between the tapering portion and the needle shielding cap, and the multichamber syringe holder is brought into the region of the first holding portion so that the at least one engagement member is prevented from moving out of the engagement with the tapered portion transversely to the longitudinal axis, away from or outward from the longitudinal axis. In this case, the multichamber syringe holder may be moved axially relative to the housing in the distal direction in such a way that the cam of the multichamber syringe holder latches from the first recess into the second recess of the housing. The multichamber syringe holder may move from the pre-mounted position to the initial position. The first holding portion of the housing, such as a sleeve inner surface of the first holding portion, may rest against an outer surface or an outer circumference of the engagement member of the multichamber syringe holder.

The at least one engagement member may be resiliently formed such as on an arm on the syringe holder, where the multichamber syringe is inserted via the proximal end with the injection needle leading into the multichamber syringe holder, which may be sleeve-shaped, where the needle shielding cap deflects the at least one engagement member transversely outward with respect to the longitudinal axis, e.g., away from the longitudinal axis, where, when the needle shielding cap has been moved completely past the at least one engagement member, the at least one engagement member snaps into the gap between the tapering region and the needle shielding cap. Subsequently, the multichamber syringe holder may be moved with the syringe into engagement with the first holding portion of the housing of the autoinjector, where the at least one engagement member is held in the engagement with the gap between the needle shielding cap and the tapering portion is blocked against radial deflection and can no longer spring out of said engagement.

In alternative embodiments, the engagement member may be configured so as to be fixed in such a way that it cannot move away from the longitudinal axis transversely to the longitudinal axis. The housing may thus have no first holding portion for holding the engagement element.

In embodiments, the multichamber syringe holder may not include an engagement member, e.g., it may not include a shoulder, in order to hold the multichamber syringe for instance in the distal direction. The distal stop of the multichamber syringe holder may instead hold the multichamber syringe for instance in the distal direction. As a result, a displacement of the needle shielding cap of the injection needle can be prevented, so that the sterility of the injection needle is not impaired.

A pull-off cap may be attached to the distal end of the autoinjector or the housing of the autoinjector and close or cover the distal end of the housing. The pull-off cap may, for example, be connected by a snap-fit to the housing in a friction-locking and/or positive-locking manner. The pull-off cap may, for example, be removable from the autoinjector, such as from the housing, during removal from the autoinjector or the housing with an axial movement or a combined axial/rotational movement.

The pull-off cap, which may be detachably provided at the distal end of the housing of the autoinjector, may include one or more engagement elements in order to cause the removal of the needle shielding cap from the multichamber syringe when the pull-off cap is removed from the autoinjector. The pull-off cap, which may be coupled to the engagement element, may be connected to the needle shielding cap via the engagement element in such a way that the removal of the pull-off cap from the autoinjector causes the removal of the needle shielding cap from the multichamber syringe. In particular, at least a part of the movement or the entire movement of the pull-off cap may be transmitted to the engagement element in the distal direction, e.g., the engagement element may be entrained by the pull-off cap, so that the engagement element pulls off the needle shielding cap from the multichamber syringe, in particular the needle holding portion. The engagement element may be configured such that the engagement element can engage with the needle shielding cap or can be in engagement with the needle shielding cap in order to remove the needle shielding cap from the multichamber syringe. A movement of the pull-off cap in the distal direction causes the needle shielding cap to be entrained, where the needle shielding cap is removed from the product container. The engagement element engages on or in the needle shielding cap. The engagement element may engage on or in a sleeve surface or on or in an edge or on or in a distal end face or on or in a proximal end face of the needle shielding cap. The engagement element may be of a hook-shaped configuration.

The pull-off cap may include a sleeve, where the sleeve can at least partially comprise the engagement element. The engagement element may be axially movable or may be axially fixed to the sleeve. The sleeve may be made of plastic. The engagement element may be made of metal. The sleeve may, for example, be connected to the housing of the autoinjector in a friction-locking and/or positive-locking manner, for example a snap-fit engagement. The sleeve may be removable from the autoinjector, for example the housing, during, for example, the removal of the pull-off cap from the autoinjector or the housing, with an axial movement or a combined axial/rotational movement.

When the multichamber syringe holder entrained by the multichamber syringe is moved axially into the initial position in the distal direction, the engagement element of the pull-off cap may reach the region of a second holding portion of the housing of the autoinjector. The second holding portion of the housing, in particular a sleeve inner surface of the second holding portion, may rest against an outer surface or an outer circumference of the engagement element of the pull-off cap. The second holding portion of the housing serves to prevent a movement of the engagement element transverse to the longitudinal axis from the longitudinal axis. When the pull-off cap moves in the distal direction, it may thus be ensured that the engagement element of the pull-off cap remains in engagement with the needle shielding cap of the multichamber syringe. The engagement element may engage on or in a sleeve surface or on or in an edge or on or in a distal end face or on or in a proximal end face of the needle shielding cap.

The engagement element of the pull-off cap may include one or more snap-in hooks and one or more catches. The catch may be arranged on the snap-in hook, where the catch may engage on or in a sleeve surface or on or in an edge or on or in a distal end face or on or in a proximal end face of the needle shielding cap.

In alternative embodiments, the first and second holding portions of the housing may be formed in one piece.

The first and/or the second holding portion of the housing may be sleeve-shaped and arranged inside the housing. A stop for limiting the axial movement of the needle shielding sleeve in the proximal direction can be provided between the sleeve-shaped first and/or second holding portion of the housing and the sleeve-shaped housing. The holding portion of the housing may project beyond the distal end of the housing in the distal direction. Furthermore, the first and/or second holding portion may have one or more grooves which, in conjunction with the rail or rails provided on the needle shielding sleeve, form an anti-rotation lock between the housing and the needle shielding sleeve. The rail of the needle shielding sleeve may be provided on a sleeve inner surface of the needle shielding sleeve. The groove of the holding portion may be arranged on a sleeve outer surface of the holding portion. The needle shielding sleeve may be axially moved in a rotationally fixed manner between the holding portion of the housing and the housing. In alternative embodiments, the one or more grooves may be provided on the needle shielding sleeve and the one or more rails may be provided on the holding portion of the housing in order to form a locking connection between the housing and the needle shielding sleeve. The groove of the needle shielding sleeve may be provided on a sleeve inner surface of the needle shielding sleeve. The rail of the holding portion may be arranged on a sleeve outer surface of the holding portion.

In alternative embodiments, the engagement element may be configured such that the engagement element of the pull-off cap remains in engagement with the needle shielding cap of the multichamber syringe. For example, the thickness of the metal of the engagement element of the pull-off cap may be selected such that the engagement element remains in engagement with the needle shielding cap. Thus, the housing may not include a second holding portion, in particular it may not include a sleeve inner surface of the second holding portion for resting against an outer surface or an outer circumference of the engagement element of the pull-off cap.

In embodiments, the multichamber syringe holder may include at least one projection which is arranged resiliently, for instance arranged on an arm and, for example, distally from the cam for fastening the multichamber syringe holder to the housing. The at least one projection may inhibit or prevent a needle shielding sleeve from moving from its initial position into its actuated position in such a way that when a limit force exerted on the needle shielding sleeve along the longitudinal axis L of the autoinjector is exceeded, the at least one projection is pressed out of the engagement with the needle shielding sleeve, whereby the needle shielding sleeve may be abruptly moved into its actuated position relative to the housing.

The autoinjector may further include a drive element which acts on the plunger at least during the discharge of the product, in particular rests against the plunger and a first spring which acts on the drive element such as, for example, bracing in particular with its distal end against the drive element. The drive element may, for example, be sleeve-shaped. Furthermore, the drive element may include a rib which may be arranged, for example, in the region of the distal end of the drive element. The distal end of the first spring may brace against the rib. The rib may extend in the proximal direction. The rib may be provided in the interior of the drive element. The rib of the drive element may be provided, for example, on an inner side of the drive element. The first spring may be arranged within the sleeve-shaped drive element. The rib of the drive element may serve to adjust the spring tension of the first spring. For example, a longer rib may generate a higher spring bias. The rib may be configured such that the spring tension of the first spring is biased or is such that the liquid product or the plurality of products may be discharged from the multichamber syringe. The first spring may be biased so strongly that it can discharge the liquid product or the plurality of liquid products from the multichamber syringe, in particular from the second chamber of the multichamber syringe, by moving the drive element by a discharge stroke. The force of the first spring may be dimensioned such that, in one embodiment of the present disclosure, the liquid product may flow out of the first chamber of the multichamber syringe via the bypass into the second chamber in order to then be mixed with the liquid product in the second chamber, and then the mixed product discharged from the second chamber of the multichamber syringe. In another embodiment of the present disclosure, the force of the first spring may be dimensioned such that first the liquid product can be discharged from the second chamber of the multichamber syringe, and thereafter the liquid product can flow out of the first chamber of the multichamber syringe via the bypass into the second chamber in order to then be able to be discharged from the second chamber. The axial arrangement of the bypass in the syringe body influences whether a mixed product is to be administered or whether a sequential administration of several products is to be done. In addition, the force of the first spring may be dependent on the internal diameter of the injection needle (needle gauge), the inside diameter of the bypass and the viscosity of the liquid products and/or the frictional force between the two plungers and the syringe body.

The rib may also serve to reinforce the drive element, such as the part of the drive element against which the first spring braces. This may make it possible to prevent the drive element from being damaged, in particular being fractured by the spring force of the first spring. The first spring may be a helical spring which acts as a compression spring and may be formed of metal. The first spring may be biased strongly enough, in particular in the delivery state of the autoinjector, that it or the energy stored therein may be sufficient to discharge the product from the multichamber syringe, such as from the second chamber of the multichamber syringe, substantially completely by moving the drive element by a discharge stroke. The movement of the drive element by the discharge stroke may also cause the two plungers or the first plunger to be moved. If, in the delivery state, there is a distance between the first plunger and the drive element, the discharge stroke of the plungers is smaller than the discharge stroke of the drive element, which is because the first plunger remains unloaded until use, whereby an undesired premature discharge of the product is avoided. In principle, however, it may also be possible for the drive element to rest against the first plunger in the delivery state and not just during the discharge of the product. If the drive element is already resting on the first plunger in the delivery state, the discharge stroke of the two plungers and of the first plunger corresponds to the discharge stroke of the drive element. The proximal end of the first spring, which can also be referred to as a discharge spring due to its function, may brace against the housing or an element fixed to the housing, such as an element that is axially fixed to the housing only temporarily.

According to the present disclosure, the autoinjector may include a signal member, a signal stop and a second spring. The second spring may exert a spring force acting on the signal member counter to the discharge direction or in the proximal direction. For instance, the second spring may brace with its proximal end against the signal member.

The second spring can may, for example, be a helical spring acting as a compression spring, which may brace with its proximal end against the signal member. The second spring may be constructed of metal. The second spring may brace with its distal end, for example, against the housing or an element fixed to the housing. The distal end of the second spring may brace against the needle shielding sleeve or an element which, for instance when the needle shielding sleeve is moved relative to the housing, is moved with the needle shielding sleeve. For example, the element may be a switching module or a switching sleeve as described further herein. The element may be arranged kinematically and/or geometrically between the needle shielding sleeve and the distal end of the second spring. Here, the needle shielding sleeve may be movable from its actuated position into the needle shielding position by means of the second spring. The spring may thus perform a dual function, because it may additionally exert the aforementioned force on the signal member.

For instance, in the delivery state or during a first partial stroke of the discharge stroke of the drive element, the signal member may be coupled to the drive element in an axially fixed manner, so that the signal member is movable with the drive element along the longitudinal axis and in particular in the distal direction relative to the housing. The axially fixed coupling to the drive element causes the signal member to be entrained during the displacement of the drive element in the discharge direction, in particular during the execution of the first partial stroke of the discharge stroke, and may cause the second spring to be tensioned. During a second partial stroke of the discharge stroke, it is that the axially fixed coupling between the signal member and the drive element may be released. The axially fixed coupling between the signal member and the drive element may thus be releasable. If the axially fixed coupling between the signal member and the drive element is released—and there are in particular no further couplings between the signal member and a further element, as will be described further herein—the signal member may be able to be accelerated counter to the discharge direction and relative to the drive element and/or the housing by means of the second, biased spring. Due to the entrainment of the signal member by the drive element by the first partial stroke, a distance, which extends, for example, along the longitudinal axis, is formed between the signal stop and the signal member, said distance in particular corresponding to the first partial stroke. The second spring may accelerate the signal member at this distance, whereby the signal member impinges on the signal stop at a speed such that a pulse is output to the signal member, which pulse generates an acoustic (audible) and/or tactile signal.

The signal stop may be formed by the housing or by an element which is at least axially fixed thereto, may also be connected to the housing in a rotationally fixed manner. For example, this element may be a closure cap at the proximal end of the housing and/or form the proximal end of the autoinjector. The closure cap may be connected to the housing, may be connected in a positive-locking manner, or alternatively connected in a friction-locking or integral manner. The element may be locked to the housing. A separate closure cap may have the advantage that the installation of the device is facilitated, where for the installation at least a portion of the components is introduced into the housing via the proximal end, which may then be sealed off with the closure cap. The closure cap may form a resonance body when the signal stop is arranged on the closure cap, where the auditory impression of the acoustic signal can be changed within certain limits by the configuration of material thicknesses and shapes of the closure cap.

In embodiments, the signal member may include a first engagement member, which may be resilient or/and may be arranged on a resilient arm, which member may releasably engage in the drive element, in particular in a recess of the drive element. As a result, the drive element may be coupled to the signal member in an axially fixed manner, where the axially fixed coupling between the drive element and the signal member is released when the signal member, such as the first engagement member, is disengaged or pressed out of the engagement with the drive element, such as the recess of the drive element.

In particular, the first engagement member may be released from the engagement with the drive element at the end of the first partial stroke of the drive element.

The signal stop may be arranged along the longitudinal axis of the autoinjector such that it is arranged in alignment with the signal member. This causes the signal member to hit the signal stop with a movement along the longitudinal axis of the autoinjector.

In embodiments having a needle shielding sleeve, the needle shielding sleeve may acts on the second spring, where the needle shielding sleeve can be moved, in particular by the actuating stroke, from its initial position relative to the housing and along the longitudinal axis of the auto-injector in the proximal direction (e.g., counter to the discharge direction), in order to trigger the discharge of the product. As a result, the second spring may be tensioned, and the discharge of the product, e.g., by a movement of the drive element in the discharge direction, may be triggered. The needle shielding sleeve may be moved from its initial position by the actuating stroke into its actuated position in that its distal end may be pressed against the puncture site of the patient, where the housing is moved relative to the needle shielding sleeve in the direction of the puncture site, so that the needle shielding sleeve executes the actuating stroke relative to the housing. In this case, the injection needle protruding from the distal end of the needle shielding sleeve may also be inserted into the puncture site. After the discharge of the product has been carried out, in particular after a short waiting time, for example 3 to 10 seconds, after which the signal has been generated by means of the signal member, the autoinjector may be removed from the puncture site, where the needle shielding sleeve may be moved by the needle shielding stroke relative to the housing from its actuated position into the needle shielding position, such as by means of the spring energy stored in the second spring. By removing the autoinjector from the puncture site, the injection needle may also be pulled out of the puncture site.

In certain embodiments, a switching module may be arranged kinematically between the second spring and the needle shielding sleeve, where the switching module is entrained by the needle shielding sleeve in the proximal direction when the needle shielding sleeve is moved from its initial position in the proximal direction or into the actuated position, and moves the needle shielding sleeve in the distal direction when the spring acting on the switching module moves the switching module in the distal direction. The switching module or a part thereof, for example a switching sleeve, may be integrally connected with the needle shielding sleeve or, for example, connected in a positive-locking manner, for example snap-fit, or loosely resting against the needle shielding sleeve. The switching module may be a single part or may include a plurality of parts, where a multi-part switching module may include at least the switching sleeve and a locking sleeve. The locking sleeve may be movable relative to the needle shielding sleeve and/or switching sleeve, for example along the longitudinal axis. For example, the second spring may brace against the switching sleeve and the switching sleeve against the needle shielding sleeve. In alternative embodiments, the switching sleeve and the needle shielding sleeve may be connected in an axially fixed manner and may also be connected in a rotationally fixed manner, where the second spring can be braced against the switching sleeve. In alternative embodiments, the switching sleeve and needle shielding sleeve may be formed in one piece, where the second spring can be braced against the switching sleeve. Between the locking sleeve and the switching sleeve, an acting lock member (for example, a unidirectionally acting locking member) may be provided which the aforementioned locking member that may lock the needle shielding sleeve in its needle shielding position and is formed (for example, by the locking sleeve and engages in the switching sleeve) in a recess. The locking member may be configured such that the switching sleeve during its movement relative to the housing in the proximal direction, entrains the locking sleeve via the locking member, such as during a movement of the needle shielding sleeve out of its initial position into an actuated position and, during its movement relative to the housing in the distal direction relative to the locking sleeve, is moved into a locking position, such as during the movement of the needle shielding sleeve from its actuated position into the needle shielding position, where in the locking position the locking member or another locking member, such as the further aforementioned one, blocks a movement of the switching sleeve relative to the locking sleeve in the proximal direction. This may prevent the needle shielding sleeve from being pushed back into the housing from its needle shielding position for renewed release of the needle tip.

For example, the switching sleeve may include a first recess in which the locking member of the locking sleeve engages releasably when the needle shielding sleeve is moved out of its initial position into its actuated position. For example, the switching sleeve may include a second recess in which the locking member or possibly the other locking member engages when the needle shielding sleeve is in its needle shielding position.

The first and second recess may be arranged at a distance, which may approximately correspond to the needle shielding stroke, along the longitudinal axis. Of course, a reversal of the arrangement of the recesses and of the locking member or of the locking members may also be possible, e.g., the at least one locking member may be formed on the switching sleeve and the at least one recess, e.g., the first recess and, where applicable, the second recess on the locking sleeve.

In alternative embodiments, the switching sleeve may include a first recess in which the locking member or locking members of the locking sleeve engage(s) releasably when the needle shielding sleeve is moved from its initial position into its actuated position. The locking member of the locking sleeve may hit the proximal end of the switching sleeve when the needle shielding sleeve is in its needle shielding position. Of course, a reversal of the arrangement of the recess and the locking member is also possible.

The locking member and, where applicable, the other locking member may be arranged resiliently, in particular in each case on a resilient arm. The switching sleeve may surround and/or guide the locking sleeve.

In embodiments, the signal member may include a second engagement member, which may be moved into an, in particular axially fixed, engagement with the needle shielding sleeve or the switching module, in particular the locking sleeve, by the disengagement movement of the first engagement member with which the first engagement member moves out of the drive element. The first engagement member and the second engagement member of the signal member may be matched to one another in such a way that the second engagement member already engages, maybe in an axially fixed manner, in the needle shielding sleeve or the switching module when the first engagement member is not yet completely released from the engagement with the drive element. This may reliably prevent the first engagement member from being released from the engagement with the drive element already when the second engagement member is not yet in the engagement with the needle shielding sleeve or the switching module, in particular the locking sleeve. The needle shielding sleeve or the switching module, in particular the locking sleeve, may include a further recess, for example, into which the second engagement member of the signal member engages, for example for the axially fixed coupling between the signal member and the switching module, in particular the locking sleeve or the needle shielding sleeve. The drive element may include a recess in which the first engagement member engages for the axially fixed coupling between the drive element and the signal member. The first engagement member and the second engagement member may be formed on a common elastic arm, where the first engagement member points, for example, radially toward the longitudinal axis and the second engagement member points, for example, radially away from the longitudinal axis. The first and second engagement members may be arranged radially, for instance, between the drive element and the needle shielding sleeve or the switching module, such as the locking sleeve.

During the discharge stroke of the drive element, at the end of the first partial stroke, the first engagement member of the signal member may be released from the engagement with the drive element, and, at the same time, the second engagement member of the signal member may be brought into engagement with the switching module or the needle shielding sleeve, with a movement transverse to the longitudinal axis. The drive element, by virtue of its movement in the discharge direction, may press the first engagement member out of the recess of the drive element and the second engagement member into the recess of the needle shielding sleeve or the switching module, such as the locking sleeve.

In embodiments, the needle shielding sleeve or the switching module, such as the locking sleeve, may hold the first engagement member of the signal member in the engagement with the recess of the drive element, where the recess for the second engagement member of the signal member is moved toward the second engagement member by moving the needle shielding sleeve from its initial position into its actuated position, where the recess in the actuated position of the needle shielding sleeve, for instance in the instant at which the discharge stroke is enabled, is arranged at a distance along the longitudinal axis, which may correspond approximately to the first partial stroke of the signal member, from the second engagement member. The drive element enabled for the discharge stroke by the actuation of the needle shielding sleeve may then be movable by the first partial stroke in the discharge direction. The first engagement member may be held in the engagement with the drive element by the inner circumference of the needle shielding sleeve or of the switching module, in particular of the locking sleeve, against which the second engagement member rests. The second engagement member may be located at the end of the first partial stroke relative to the longitudinal axis at the same position as the recess, where the second engagement member may engage in its recess and move the first engagement member out of its recess.

The discharge stroke of the drive element may include two phases, namely the first partial stroke and the second partial stroke. During the first partial stroke, the first engagement member of the signal member may be in the axially fixed engagement with the drive element and the second engagement member of the signal member may be out of the axially fixed engagement with the needle shielding sleeve or the switching module, in particular the locking sleeve. During the second partial stroke of the discharge stroke, the second engagement member may be in the axially fixed engagement with the needle shielding sleeve or with the switching module, such as the locking sleeve, where the first engagement member is out of the engagement with the drive element, whereby it may be brought about that the drive element is movable relative to the signal member in the distal direction by means of the first spring and/or the signal member is not yet released for the signal triggering.

In alternative embodiments, the discharge stroke may include three phases, in particular a further partial stroke. During the first partial stroke, the drive element may move axially relative to the signal member. During the first partial stroke, the signal member is not charged. During the second partial stroke, the first engagement member of the signal member may be in the axially fixed engagement with the drive element and the second engagement member of the signal member may be out of the axially fixed engagement with the needle shielding sleeve or the switching module, such as the locking sleeve. During the second partial stroke, the signal member is charged. During the third partial stroke of the discharge stroke, the second engagement member may be in the axially fixed engagement with the needle shielding sleeve or the switching module, such as the locking sleeve, where the first engagement member may be out of the engagement with the drive element, where it may be advantageously brought about that the drive element is movable relative to the signal member in the distal direction by means of the first spring and/or the signal member is not yet enabled for the signal triggering.

Generally the drive element may be movable relative to the signal member in the distal direction by means of the first spring, in particular by the second partial stroke, when the first engagement member of the signal member is out of the engagement with the drive element and the second engagement member of the signal member is in the engagement with the needle shielding sleeve or the switching module.

In embodiments, the second engagement member of the signal member and the recess for the second engagement member may be arranged in the delivery state of the autoinjector along the longitudinal axis approximately at the distance from each other which may be approximately the sum of the actuating stroke of the needle shielding sleeve and the first partial stroke of the drive element, which approximately corresponds to the stroke of the signal member away from the signal stop.

The drive element may prevent the second engagement member of the signal member from moving out of the axially fixed engagement with the needle shielding sleeve or the switching module when the drive element moves relative to the signal member in the distal direction, such as during the second partial stroke of the drive element. The drive element may allow the second engagement member at the end of the discharge stroke or the second partial stroke to move out of the engagement with the needle shielding sleeve or the switching module. If the second engagement member is moved out of the engagement with the needle shielding sleeve or the switching module at the end of the second partial stroke, the signal member may be accelerated by the second spring counter to the discharge direction and hits against the signal stop. The second engagement member may be held in the engagement with the needle shielding sleeve or the switching module by the outer circumference of the drive element, against which the first engagement member rests.

In embodiments, the autoinjector may include a holding element against which, for example, one end of the first spring, such as the proximal end of the first spring, braces. Alternatively, the proximal end of the spring may brace against the housing or against an element fixed to the housing. The holding element itself may be arranged fixed to the housing or movably in relation to the housing. The holding element may include a first engagement element which, before the triggering of the discharge of the product, may engage in the drive element, where the drive element is prevented from moving relative to the holding element and/or the housing in the discharge direction. The engagement of the first engagement element in the drive element is releasable for the discharge of the product. When the engagement is released, the drive element may be enabled for the movement in the discharge direction. The first spring may move the drive element relative to the holding element and/or the housing by the discharge stroke in the discharge direction. The drive element may include a recess for the first engagement element of the holding element, where this coupling between the drive element and the holding element is released when the holding element, for instance the first engagement element, is moved out of the engagement with the drive element, for instance the recess of the drive element. In this example, the first engagement element may thereby be released from the engagement with the drive element in that the needle shielding sleeve is moved from the initial position by the actuating stroke into the actuated position. For example, the first engagement element may be held by the needle shielding sleeve or the switching module, such as the locking sleeve, in the axially fixed engagement with the drive element when the needle shielding sleeve is not in its actuated position or in its initial position. For example, an inner circumference of the needle shielding sleeve or of the switching module, in particular of the locking sleeve, can hold the first engagement element in the engagement with the drive element, where, for example, a second engagement element, which is described further below, can rest against the inner circumference.

By moving the needle shielding sleeve into its actuated position, the needle shielding sleeve or the switching module, such as the locking sleeve, can allow the first engagement element of the holding element to be moved out of the engagement with the drive element, such as with a movement transverse to the longitudinal axis of the autoinjector. For example, a recess, for the second engagement element of the holding element, which may be formed on the needle shielding sleeve or the switching module, e.g., of the locking sleeve, may be arranged in the same position in relation to the longitudinal axis, like the first and/or second engagement element, so that the first engagement element can move out of the engagement with the drive element. For example, the drive element may press the first engagement element out of the engagement with the drive element when the needle shielding sleeve is in its actuated position.

The first engagement element of the holding element may, for example, point radially toward the longitudinal axis and/or be arranged on a resilient arm of the holding element.

As mentioned, the holding element may include a second engagement element, which may be movable by a disengagement movement of the first engagement element out of the drive element into an axially fixed engagement with the needle shielding sleeve or the switching module, such as the locking sleeve. The second engagement element may, for example, be arranged on the arm on which the first engagement element is arranged and/or, for example, may point radially away from the longitudinal axis. The first engagement element and the second engagement element may be matched to one another in such a way that the second engagement element already engages axially fixedly in its recess, which may formed by the needle shielding sleeve or the switching module, such as the locking sleeve, when the first engagement element is not yet completely released from the engagement with the drive element. As a result, first the axially fixed connection between the holding element and the needle shielding sleeve or the switching module may be established before the axially fixed connection between the holding element and the drive element is released, and thus a renewed or further pushing back of the needle shielding sleeve may be blocked.

For instance, when the second engagement element of the retaining element is in its recess, the drive element may be permitted to move in the distal direction relative to the holding element, for instance due to the energy stored in the biased spring. The drive element may prevent the second engagement element from moving out of the axially fixed engagement with the needle shielding sleeve or the switching module, for instance the locking sleeve, when the drive element moves relative to the signal member in the distal direction. This also applies at the end of the discharge stroke, such as when the second engagement member of the signal member is released from its recess in order to be accelerated by the second spring counter to the discharge direction.

In embodiments in which the recess for the second engagement element of the holding element is formed by the needle shielding sleeve or the switching sleeve, the second engagement element may move out of its recess at the end of the discharge stroke in order to be able to move the needle shielding sleeve from the actuated position into the needle shielding position after the product has been administered. For this purpose, the drive element may include a recess into which the first engagement element can engage, where the second engagement element simultaneously moves out of its recess in order to enable the movement of the needle shielding sleeve in the distal direction.

In embodiments including a switching module having a switching sleeve and a locking sleeve, the second engagement element may also remain at the end of the discharge stroke such that the second engagement element prevents the locking sleeve from being moved in the distal direction relative to the housing and/or the second engagement element, where the switching sleeve and/or the needle shielding sleeve can be moved in the distal direction relative to the locking sleeve, for instance due to the energy stored in the second spring, where the needle shielding sleeve is moved into its needle shielding position. As provided herein and noted for the sake of completeness, the locking member may enter into engagement between the locking sleeve and the switching sleeve, which may prevent the switching sleeve from being movable relative to the locking sleeve in the proximal direction. A movement of the locking sleeve in the proximal direction may be prevented by the locking sleeve hitting either against the housing or against an element fixed to the housing, such as, for example, on a mechanism holder or the signal member.

BRIEF DESCRIPTION OF THE DRAWINGS

FIGS. 2*a*, 2*b* and 2*c* are sectional views running through the longitudinal axis of the device, and where the sectional views are angularly offset with respect to the longitudinal axis;

DETAILED DESCRIPTION

Figure 1A:
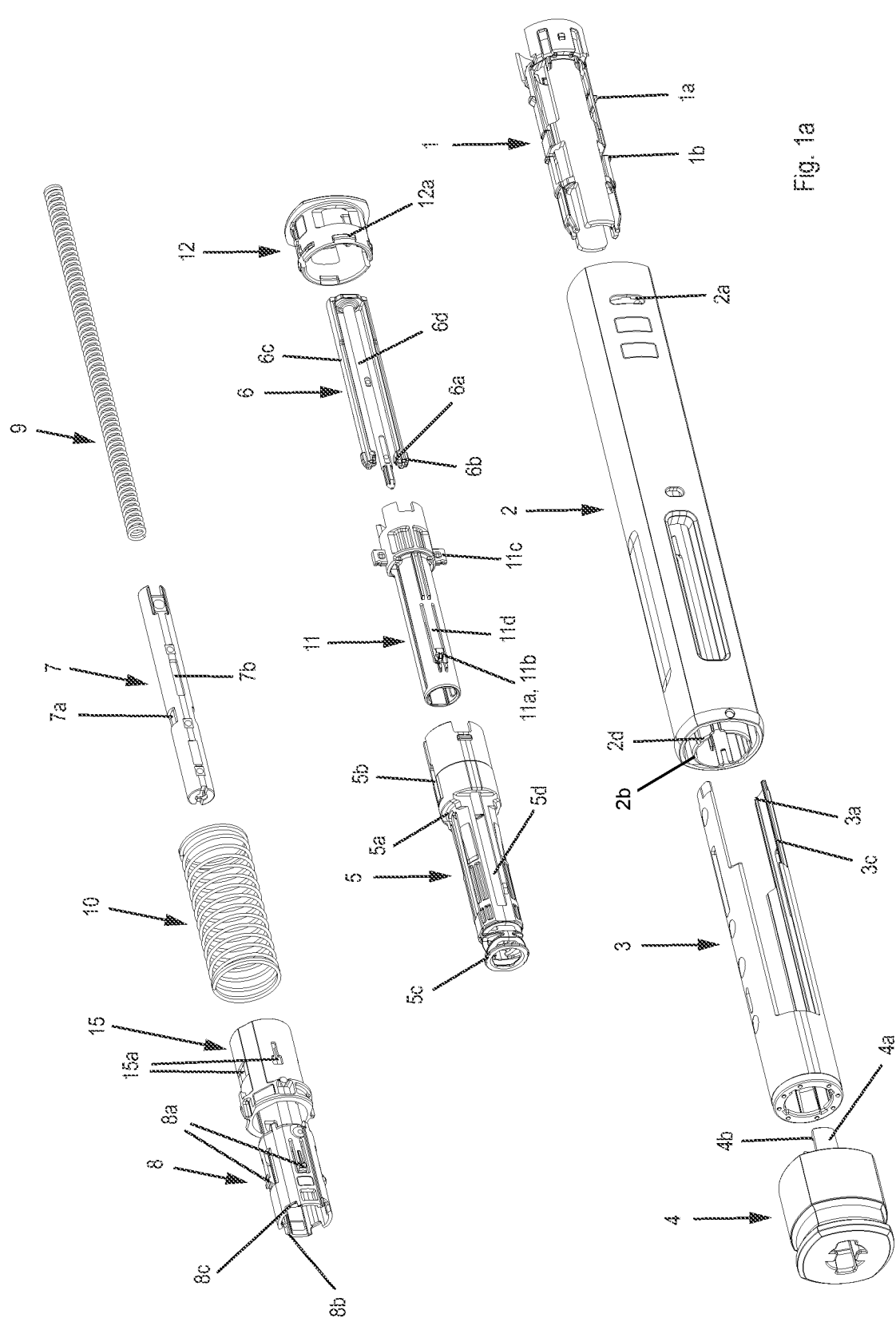
FIGS. 1*a*-1*b* show exploded isometric views of the autoinjector according to the present disclosure.
Figure 1B:
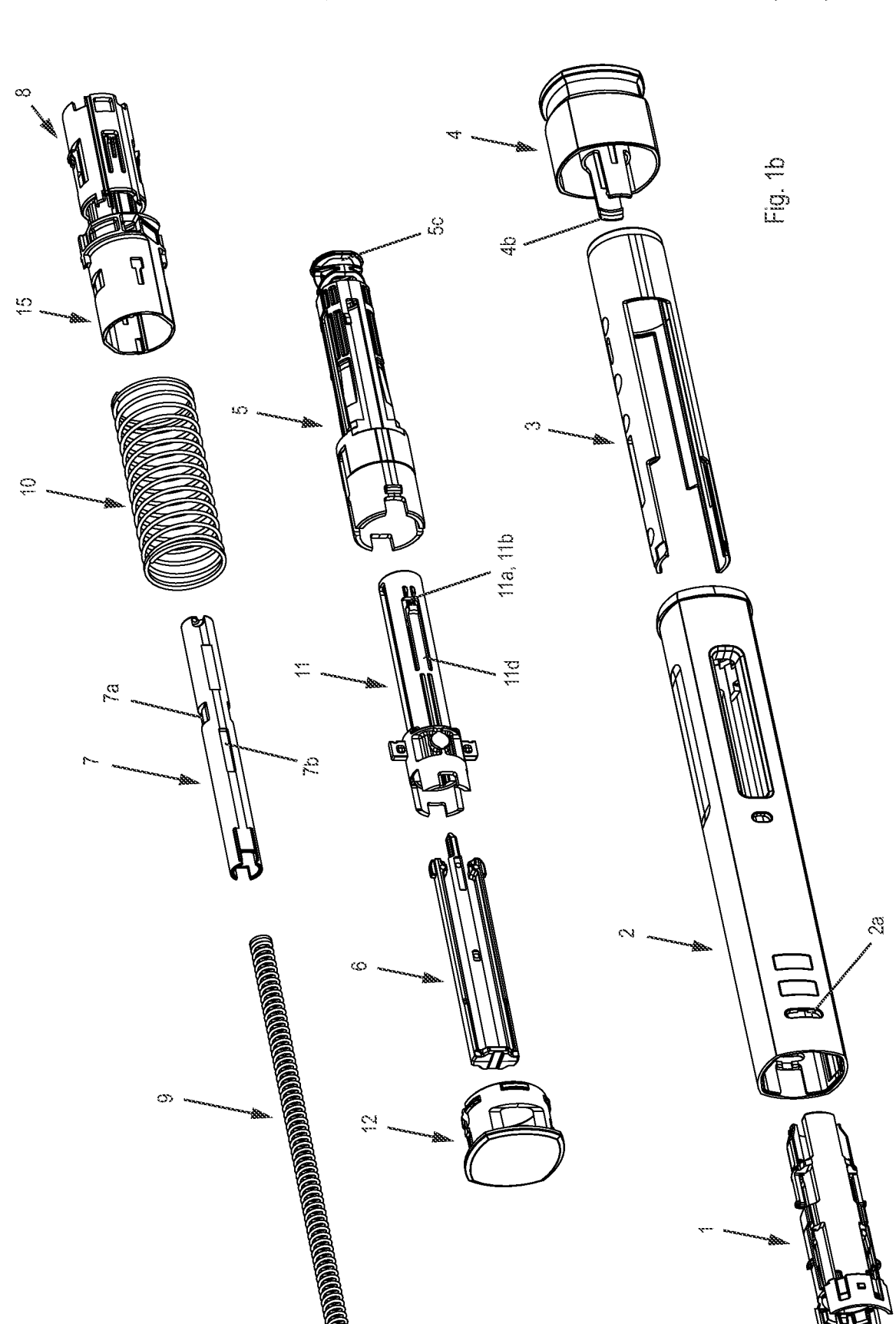

The term "distal" used herein refers to the direction in which the tip of the injection needle points. The term "proximal" used herein refers to the direction counter to the distal direction.

Referring now to FIGS. 1*a*-7*c*, the structural features and the function of the autoinjector are described.

The autoinjector includes a sleeve-shaped, elongated housing 2 with a longitudinal axis L (FIG. 2*a*), which has a closure cap 12 at its proximal end, which closure cap is positively connected to the housing 2 in a rotationally and axially fixed manner and forms the proximal end of the autoinjector. The closure cap 12 may be snap-fit to the housing 2. For this purpose, the closure cap 12 may include a latching member 12*a* which may be latched into a recess 2*a* on the housing 2, in such a way that the closure cap 12 cannot be detached or cannot be easily detached from the housing 2.

On the distal end of the autoinjector, in its delivery state (e.g., FIGS. 2*a*, 2*b*, 2*c*) a pull-off cap 4 may be arranged and may be pulled off or/and turned off before the autoinjector is used, and removed.

In the housing 2 (e.g., FIGS. 2*d*, 2*e*, 2*f*), a product container in the form of a multichamber syringe 13 is accommodated in a non-movable manner with respect to the housing 2—apart from the installation of the product container of the autoinjector—along the longitudinal axis L.

The multichamber syringe 13 has a syringe body 13*c*. An injection needle 13*a* is provided at the distal end of the syringe body 13*c*. Furthermore, the syringe body 13*c* comprises a bypass 13*d*, a first chamber 13*e* for a first liquid product and a second chamber 13*f* for a second liquid product, where the two liquid products are separated from one another in the initial position by a plunger 13*b'*, also referred to as a second plunger 13*b'*. The bypass 13*d* is formed in or on the syringe body in the form of a curved section protruding radially outwardly. The bypass 13*d* serves for the fluidic connection of the first 13*e* and the second chamber 13*f*. Two plungers 13*b*, 13*b'* may be arranged axially movably in the syringe body 13*c*. The first chamber 13*e* of the syringe body 13*c* is provided between the first plunger 13*b* and the second plunger 13*b'*. The second chamber 13*f* of the syringe body 13*c* is arranged between the second plunger 13*b'* and the distal end of the syringe body 13*c*. The first plunger 13*b* may be arranged proximally to the second plunger 13*b'* in the syringe body 13*c*. The first plunger 13*b* or the first 13*b* and the second plunger 13*b'* may be axially movable in the distal direction in the syringe body 13*c* such that the liquid product arranged in the second chamber 13*f*, for instance medication, is discharged from the multichamber syringe 13 through the injection needle 13*a*. The syringe body 13*c* may include a so-called finger flange 13*g* at its proximal end, which finger flange may project radially outwardly beyond the outer circumference of the cylindrical syringe body 13*c*. Alternatively, the finger flange 13*g* may be round.

Whether a mixed liquid product is to be discharged from a multichamber syringe 13 or two liquid products are to be discharged sequentially from a multichamber syringe 13 through an injection needle 13*a* arranged on the multichamber syringe 13, depends for instance on the axial position of the bypass 13*d* or on the syringe body 13*c*. The more distally the bypass 13*d* is arranged on or in the syringe body 13*c*, or the closer the bypass 13*d* is arranged to the injection needle 13*a* provided at the distal end of the syringe body 13*c*, the more likely the liquid product provided in the second chamber 13*f* is to be administered to a patient first and thereafter the liquid product provided in the first chamber 13*e*.

For a sequential delivery of the medication from a 1 ml multichamber syringe 13 having a syringe body 13*c* with an inner diameter of approximately 6 to 7 mm, such as of approximately 6.35 mm, in a first exemplary embodiment, the second chamber 13*f* may include a second liquid having a dynamic viscosity of about 0.7 to 1.3 centipoise (cP), such as of about 1 centipoise and a volume of about 0.2 to 0.4 ml, such as of about 0.34 ml, and the first chamber 13*e* a first liquid having a dynamic viscosity of about 0.7 to 1.3 centipoise, such as of about 1 centipoise and a volume of about 0.4 to 0.6 ml, such as of about 0.57 ml, where the two liquids are fluids and have a density of about 1000 kg/m3. The length of the bypass 13*c* is about 7 to 8 mm, such as about 7.1 mm, and the inner diameter of the bypass 13*c* is about 0.7 to 0.9 mm, such as about 0.8 mm. The discharge travel up to the bypass 13*c* is approximately 10 to 11 mm, such as approximately 10.6 mm. The two plunger frictions between the first plunger 13*b* or second 13*b'* plunger and the syringe body 13*c* are each about 1 to 2 newtons (N), such as about 1.6 newtons. The length of the injection needle 13*a* may be approximately 18 to 20 mm, such as approximately 19 mm, and configured as a normal-walled 29-gauge needle having an internal diameter of approximately 0.14 to 0.15 mm, such as approximately 0.143 mm. The sequential discharge time of the two liquids from the multichamber syringe 13 is approximately 5 to 15 seconds, such as approximately 9 to 10 seconds, such as approximately 9.5 seconds when using a spring, such as a first spring 9 or discharge spring having a spring force of approximately 8 to 9 newtons, such as approximately 8.3 newtons of the autoinjector, as will be described further herein.

For a sequential delivery of the medication from a 1 ml multichamber syringe 13 having a syringe body 13*c* with an inner diameter of approximately 6 to 7 mm, such as approximately 6.35 mm, in a second exemplary embodiment, the second chamber 13*f* can have a second liquid with a dynamic viscosity of about 8 to 10 centipoise, such as of about 9 centipoise and a volume of about 0.2 to 0.4 ml, such as of about 0.34 ml, and the first chamber 13*e* can have a first liquid with a dynamic viscosity of about 8 to 10 centipoise, such as of about 9 centipoise and a volume of about 0.4 to 0.6 ml, such as of about 0.57 ml, where the two liquids are Newtonian fluids and have a density of about 1000 kg/m3. The length of the bypass 13*c* is about 7 to 8 mm, such as about 7.1 mm, and the inner diameter of the bypass 13*c* is about 0.7 to 0.9 mm, such as about 0.8 mm. The discharge travel up to the bypass 13*c* is approximately 10 to 11 mm, such as approximately 10.6 mm. The two plunger frictions between the first plunger 13*b* or second plunger 13*b'*, respectively, and the syringe body 13*c* are each about 1 to 2 newtons, such as about 1.9 newtons. The length of the injection needle 13*a* is approximately 18 to 20 mm, such as approximately 19 mm, and is configured as a thin-walled 29-gauge needle having an internal diameter of approximately 0.2 to 0.3 mm, such as approximately 0.209 mm. The sequential discharge time of the two liquids from the multichamber syringe 13 is approximately 5 to 15 seconds, such as approximately 9 to 11 seconds, such as approximately 10 seconds when using a spring, such as a first spring 9 or discharge spring with a spring force of approximately 13 to 14 newtons, such as approximately 13.7 newtons of the autoinjector, as will be described further herein.

For a sequential delivery of the medication from a 1 ml multichamber syringe 13 having a syringe body 13*c* with an inner diameter of approximately 6 to 7 mm, such as approximately 6.35 mm, in a third exemplary embodiment, the second chamber 13*f* may include a second liquid with a dynamic viscosity of about 0.7 to 1.3 centipoise, such as of about 1 centipoise and a volume of about 0.2 to 0.4 ml, such as of about 0.34 ml, and the first chamber 13*e* a first liquid with a dynamic viscosity of about 150 to 250 centipoise, such as of about 199 centipoise and a volume of about 0.4 to 0.6 ml, such as of about 0.57 ml, where the two liquids are Newtonian fluids and have a density of about 1000 kg/m3. The length of the bypass 13*c* is about 7 to 8 mm, such as about 7.1 mm, and the inner diameter of the bypass 13*c* is about 0.7 to 0.9 mm, such as about 0.8 mm. The discharge travel up to the bypass 13*c* is approximately 10 to 11 mm, such as approximately 10.6 mm. The two plunger frictions between the first plunger 13*b* or second plunger 13*b'* and the syringe body 13c are each about 1 to 2 newtons, such as about 1.6 newtons. The length of the injection needle 13a is approximately 18 to 20 mm, such as approximately 19 mm, and may be configured as a thin-walled 29-gauge needle having an internal diameter of approximately 0.2 to 0.3 mm, such as approximately 0.209 mm.

The sequential discharge of the liquids from the multichamber syringe 13 according to the second and/or the third exemplary embodiment may be possible if the dynamic viscosity of the second liquid in the second chamber 13f is equal to or smaller than the dynamic viscosity of the first liquid in the first chamber 13e. If the dynamic viscosity of the first liquid in the first chamber 13e is greater than the dynamic viscosity of the second liquid in the second chamber 13f, the viscosity ratios indicated below are not to be exceeded, so that the distal displacement of the second plunger 13b' in the region of the bypass 13c is prevented during the discharge travel of the first plunger 13b. In a first example, the first liquid in the first chamber 13e has a dynamic viscosity of about 1 centipoise (cP) and the second liquid in the second chamber 13f has a dynamic viscosity of about 199 centipoise. A viscosity ratio of approximately 199 between the first liquid of the first chamber 13e and the second liquid of the second chamber 13f is to be maintained. In a second example, the first liquid in the first chamber 13e has a dynamic viscosity of about 2 centipoise and the second liquid in the second chamber 13f has a dynamic viscosity of about 211 centipoise. A viscosity ratio of about 110 between the first liquid of the first chamber 13e and the second liquid of the second chamber 13f is to be maintained. In the case of a greater dynamic viscosity of the second liquid of approximately 2 centipoise, a viscosity ratio of approximately 110 between the first liquid of the first chamber 13e and the second liquid of the second chamber 13f should always be maintained. The ratio of the dynamic viscosity of the two liquids from the multichamber syringe 13 enables sequential discharge when a spring is used, such as a first spring 9 disclosed herein or a discharge spring having a spring force of approximately 13 to 14 newtons, such as approximately 13.7 newtons of the autoinjector, as will be described further herein.

For a sequential delivery of the medication from a 1 ml multichamber syringe 13 having a syringe body 13c with an inner diameter of approximately 6 to 7 mm, such as of approximately 6.35 mm, in a fourth exemplary embodiment, the second chamber 13f may include a second liquid with a dynamic viscosity of about 27 to 29 centipoise, such as of about 28 centipoise and a volume of about 0.2 to 0.4 ml, such as of about 0.34 ml, and the first chamber 13e a first liquid with a dynamic viscosity of about 27 to 29 centipoise, such as of about 28 centipoise and a volume of about 0.4 to 0.6 ml, such as of about 0.57 ml, where the two liquids are Newtonian fluids and have a density of about 1000 kg/m3. The length of the bypass 13c is about 7 to 8 mm, such as about 7.1 mm, and the inner diameter of the bypass 13c is about 0.7 to 0.9 mm, such as about 0.8 mm. The discharge travel up to the bypass 13c is approximately 10 to 11 mm, such as approximately 10.6 mm. The two plunger frictions between the first plunger 13b or second plunger 13b', respectively, and the syringe body 13c are each about 1 to 2 newtons, such as about 1.9 newtons. The length of the injection needle 13a is approximately 18 to 20 mm, such as approximately 19 mm, and may be configured as an especially thin-walled 27-gauge needle having an internal diameter of approximately 0.2 to 0.3 mm, such as of approximately 0.28 mm. The sequential discharge time of the two liquids from the multichamber syringe 13 is approximately 5 to 15 seconds, such as between approximately 9 and 10 seconds, such as approximately 9.7 seconds when using a spring, such as spring 9, in particular a first spring or discharge spring having a spring force of approximately 13 to 14 newtons, such as of approximately 13.7 newtons of the autoinjector, as will be described further herein.

For a sequential delivery of the medication from a 1 ml multichamber syringe 13 with a syringe body 13c having an inner diameter of approximately 6 to 7 mm, such as approximately 6.35 mm, in a fifth exemplary embodiment, the second chamber 13f may include a second liquid having a dynamic viscosity of about 0.7 to 1.3 centipoise, such as of about 1 centipoise and a volume of about 0.3 to 0.4 ml, such as of about 0.34 ml, and the first chamber 13e a first liquid having a dynamic viscosity of about 60 to 120 centipoise, such as of about 90 centipoise and a volume of about 0.5 to 0.6 ml, such as of about 0.57 ml, where the two liquids are Newtonian fluids and have a density of about 1000 kg/m3. The length of the bypass 13c is about 7 to 8 mm, such as about 7.1 mm, and the inner diameter of the bypass 13c is about 0.7 to 0.9 mm, such as about 0.8 mm. The discharge travel up to the bypass 13c is approximately 10 to 11 mm, such as approximately 10.6 mm. The two plunger frictions between the first plunger 13b or second plunger 13b', respectively, and the syringe body 13c are each about 1 to 2 newtons, such as about 1.9 newtons. The length of the injection needle 13a is approximately 18 to 20 mm, such as approximately 19 mm, and may be configured as an especially thin-walled 27-gauge needle having an internal diameter of approximately 0.2 to 0.3 mm, such as of approximately 0.28 mm.

The sequential discharge of the liquids from the multichamber syringe 13 according to the fourth and/or the fifth exemplary embodiment is possible if the dynamic viscosity of the second liquid in the second chamber 13f is equal to or smaller than the dynamic viscosity of the first liquid in the first chamber 13e. If the dynamic viscosity of the first liquid in the first chamber 13e is greater than the dynamic viscosity of the second liquid in the second chamber 13f, the viscosity ratios indicated below are not to be exceeded, so that the distal displacement of the second plunger 13b' in the region of the bypass 13c is prevented during the discharge travel of the first plunger 13b. In a first example, the first liquid in the first chamber 13e has a dynamic viscosity of about 1 centipoise, and the second liquid in the second chamber 13f a dynamic viscosity of about 90 centipoise. A viscosity ratio of about 90 between the first liquid of the first chamber 13e and the second liquid of the second chamber 13f is to be maintained. In a second example, the first liquid in the first chamber 13e has a dynamic viscosity of about 2 centipoise and the second liquid in the second chamber 13f has a dynamic viscosity of about 100 centipoise. A viscosity ratio of about 50 between the first liquid of the first chamber 13e and the second liquid of the second chamber 13f is to be maintained. In a third example, the first liquid in the first chamber 13e has a dynamic viscosity of about 3 centipoise and the second liquid in the second chamber 13f has a dynamic viscosity of about 103 centipoise. A viscosity ratio of about 34 between the first liquid of the first chamber 13e and the second liquid of the second chamber 13f is to be maintained. In the case of a greater dynamic viscosity of the second liquid of approximately 3 centipoise, a viscosity ratio of approximately 34 between the first liquid of the first chamber 13e and the second liquid of the second chamber 13f should always be maintained. The ratio of the dynamic viscosity of the two liquids from the multichamber syringe 13 enables sequential discharge when a spring is used, such as a first spring 9 disclosed herein or a discharge spring having a spring force of approximately 13 to 14 newtons, such as of approximately 13.7 newtons of the autoinjector, as will be described further herein.

The multichamber syringe 13 may be accommodated within a multichamber syringe holder 1 such that the multichamber syringe 13 is secured relative to the multichamber syringe holder 1 at least against a movement along the longitudinal axis L in the distal direction. As can best be seen from FIG. 2a, the multichamber syringe holder 1 is connected to the housing 2 in a positive-locking manner, in particular latched. For this purpose, the housing 2 has recesses in which latching members engage, the members being formed here at the proximal end of the syringe holder 1.

The multichamber syringe holder 1 can comprise a cutout 1c for the bypass 13d of the multichamber syringe 13. The cutout 1c can be formed continuously or with separations, where the cutout 1c extends in the longitudinal direction.

Figures 2A, 2B, 2C:
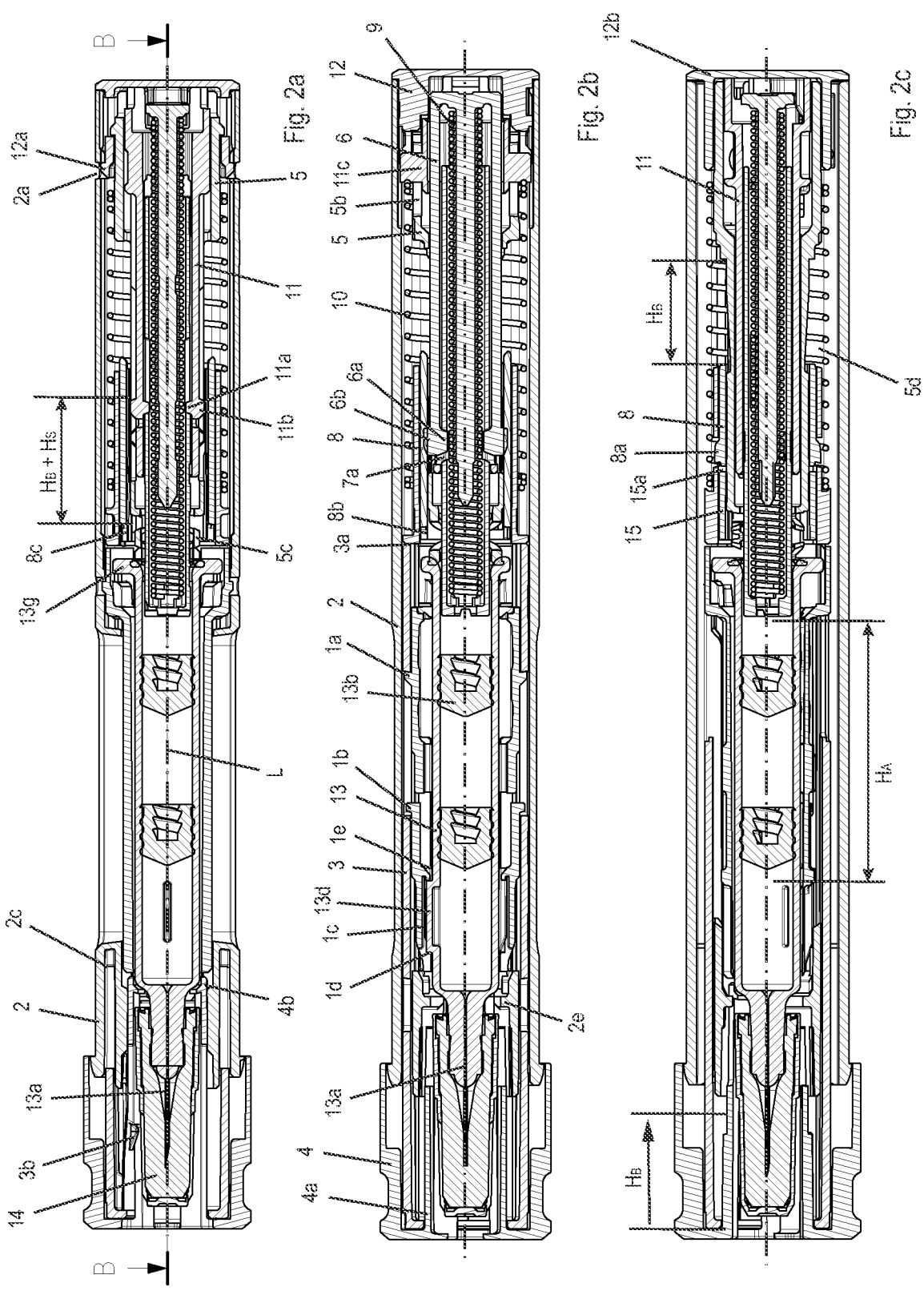
FIGS. 2*a*, 2*b* and 2*c* show the autoinjector from FIGS. 1*a* and 1*b* in a delivery state, where
Figures 2D, 2E, 2F:
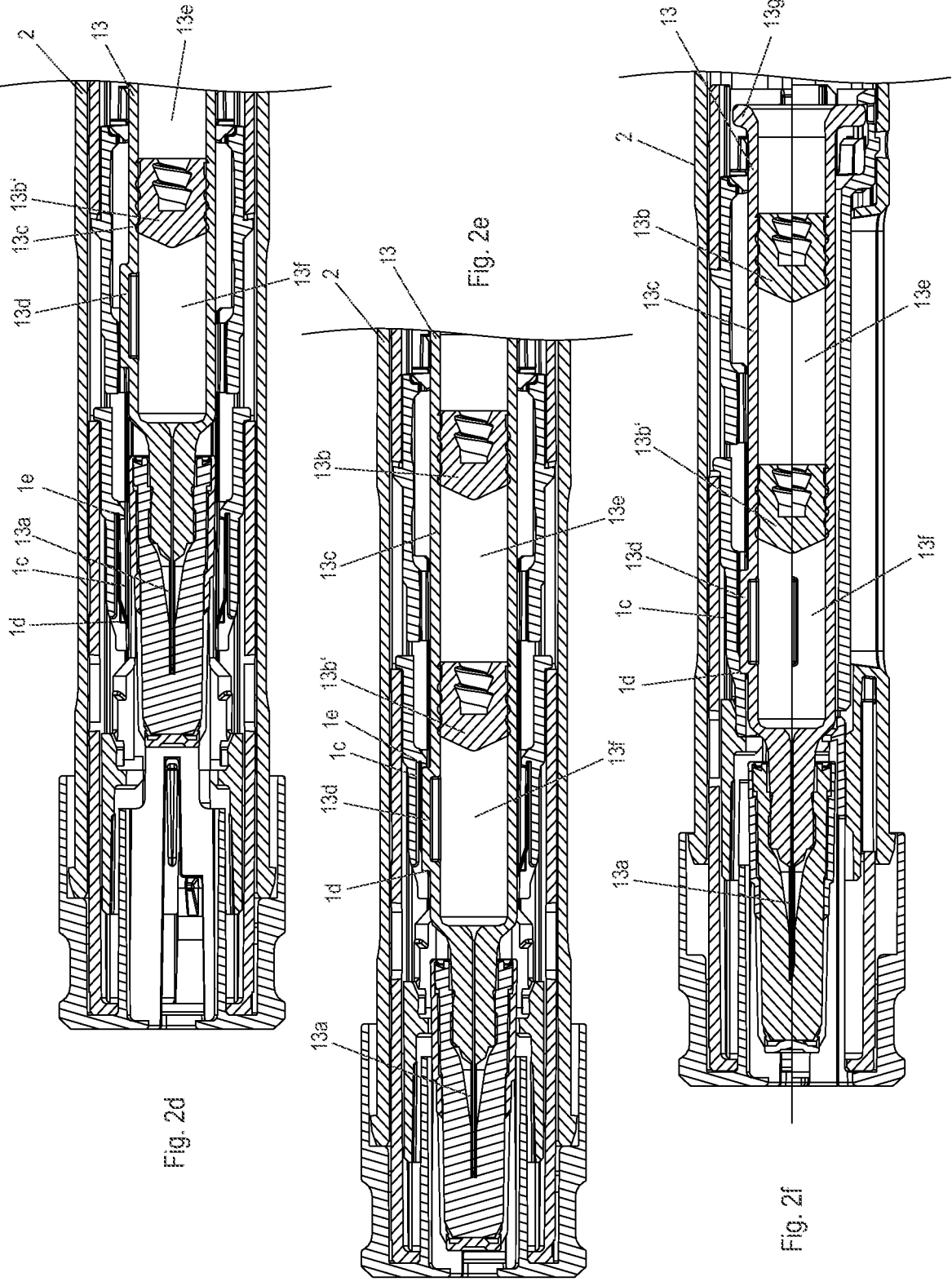
FIGS. 2*d*-2*e* show the autoinjector from FIGS. 1*a* and 1*b*, where the multichamber syringe is shown before and after insertion into the multichamber syringe holder.
FIG. 2*f* shows an alternative embodiment of the present disclosure in a delivery state, where the multichamber syringe is inserted in the multichamber syringe holder.

In embodiments, as can be seen in FIGS. 2d and 2e, the cutout 1c of the multichamber syringe holder 1 can have a distal stop 1d and a proximal stop 1e. The bypass 13d can be arranged in an axially fixed manner between the distal stop 1d and the proximal stop 1e when the multichamber syringe is inserted in the multichamber syringe holder. The proximal stop 1e, and/or the distal stop 1d and the proximal stop 1e, may be configured to be elastically and/or plastically deformable. When the multichamber syringe 13 is inserted during installation from a proximal end into the multichamber syringe holder 1, which may be connected to the housing 2 in an axially fixed manner, such as in an axially and rotationally fixed manner, as can be seen in FIG. 2e, the proximal stop 1e can deform elastically and/or plastically in such a way that the multichamber syringe 13 can be inserted into the multichamber syringe holder 1. When the multichamber syringe 13 in the multichamber syringe holder 1, as shown in FIG. 2e, is inserted in the multichamber syringe holder 1, the proximal stop 1e can deform elastically and/or plastically such that the multichamber syringe 13 is held in the multichamber syringe holder 1 at least axially in the proximal direction.

In alternative embodiments, the cutout 1c can have only a distal stop 1d, as can be seen in FIG. 2f. When the multichamber syringe 13 is inserted in the multichamber syringe holder 1, a force acting on the multichamber syringe 13, in particular on the finger flange 13g of the multichamber syringe 13 in the distal direction, can hold the multichamber syringe 13 against the distal stop 1d. In order to prevent the multichamber syringe 13 from being movable in the proximal direction relative to the multichamber syringe holder 1, the multichamber syringe 13 is pressed at its proximal end into engagement with the distal stop 1d of the cutout 1c of the multichamber syringe holder 1 by a holder acting on the syringe body 13c. The holder is formed by a retaining spring portion 5c of a mechanism holder 5. In relation to the housing 2, the mechanism holder 5 may be arranged in a non-movable and/or rotationally fixed manner along the longitudinal axis L. The sleeve-shaped mechanism holder 5 can be snap-fit to the housing 2 or alternatively to the closure cap 12. Furthermore, the retaining spring portion 5c can compensate for longitudinal differences of the product container 13, which can arise due to manufacturing tolerances, where the fixed seat of the multichamber syringe 13 at the distal stop 1d of the cutout 1c of the multichamber syringe holder 1 may be ensured.

The multichamber syringe 13 may be held in an axially fixed manner in the multichamber syringe holder 1 or elastically resiliently in the axial direction in the multichamber syringe holder 1.

The cutout 1c of the multichamber syringe holder 1 may be configured such that the multichamber syringe 13 and the multichamber syringe holder 1 are arranged in a rotationally fixed manner relative to one another. The cutout 1c of the multichamber syringe holder 1 may be configured to taper in the distal direction. The tapering in the syringe holder body may be configured to be elastically and/or plastically deformable.

In alternative embodiments, only the distal stop 1d of the cutout 1c of the multichamber syringe holder 1 may be tapered to form an anti-rotation lock between the multichamber syringe 13 and the multichamber syringe holder 1.

The multichamber syringe 13 may be arranged in relation to the housing 2 such that the needle tip protrudes distally beyond the distal end of the housing 2. In the initial or delivery state of the autoinjector, e.g., when the pull-off cap 4 is arranged on the autoinjector, the injection needle 13a may be covered by a needle shielding cap 14, which in the example shown may be configured as a so-called rigid needle shield, which is known to the person skilled in the art and known alternatively as a soft needle shield or needle shield, in order to protect the injection needle 13a from contamination or to keep the injection needle 13a and the medication sterile.

As can be seen in FIGS. 2d, 2e and 2f, the distal stop 1d of the multichamber syringe holder 1 may hold the multichamber syringe 13 in the distal direction. As a result, a displacement of the needle shielding cap 14 (FIG. 2a) of the injection needle 13a can be prevented, so that the sterility of the injection needle 13a is not impaired.

The pull-off cap 4 may be detachably snap-fit to the housing 2 or a needle shielding sleeve 3, where this snap-fit connection may be released when the pull-off cap 4 is removed from the housing 2 or the needle shielding sleeve 3. In the example shown, the snap-fit connection may be formed by a snap geometry 3b of the needle shielding sleeve 3 (FIG. 2a) and a snap-in hook 4a of the pull-off cap 4 (FIG. 2b). These snap-in hooks 4a may further secure the pull-off cap 4 against proximal movement relative to the housing 2 by their having a support fixed to the housing 2 or to a distal end face on the multichamber syringe holder 1. The pull-off cap 4 may further include on the snap-in hook 4a, at least one catch 4b which engages in a gap between the syringe body, for instance at its tapering region, and the proximal end of the rigid needle shield 14. When the pull-off cap 4 is removed from the autoinjector, the catch 4b hooks into the proximal end of the rigid needle shield 14, whereby the rigid needle shield 14 may be detached from the product container 13 and removed from the autoinjector together with the pull-off cap 4. Alternatively, the catch 4b may engage or hook into a sleeve surface of the rigid needle shield 14 or into a sleeve surface of the soft needle shield or needle shield for removal thereof.

The autoinjector has a needle shielding sleeve 3, which is movable relative to the housing 2 and along the longitudinal axis L by an actuation stroke $H_B$ (FIG. 2c) in the proximal direction into an actuated position in order to trigger discharge of the product. In the initial position of the needle shielding sleeve 3 as shown in FIGS. 2a-2c, where the pull-off cap 4 is removed, the distal end of the needle shielding sleeve 3 protrudes distally beyond the needle tip of the injection needle 13a, so that access to the needle tip is initially prevented. By moving the needle shielding sleeve 3 by the actuation stroke $H_B$, the needle shielding sleeve 3 is moved in the proximal direction to such an extent that the injection needle 13a emerges from the distal end of the needle shielding sleeve 3, in particular protrudes with a length which corresponds to the injection depth of the needle into the puncture site. The injection needle 13a should project beyond the distal end of the needle shielding sleeve 3 to such an extent that a subcutaneous injection can take place. In particular, the housing 2 can form a stop 2c on which the needle shielding sleeve 3 rests in the actuated position.

Figures 7A, 7B, 7C:
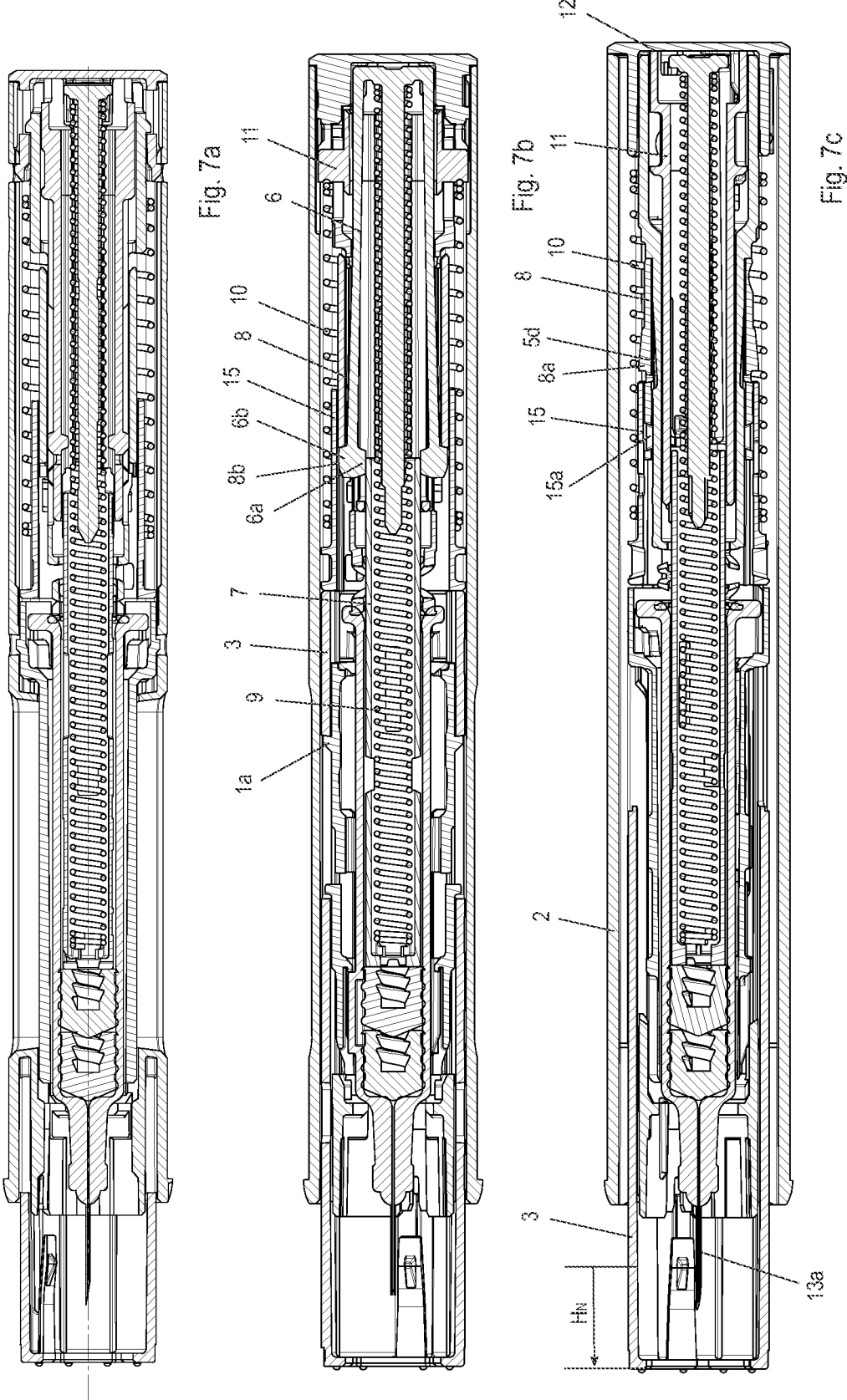
FIGS. 7*a*-7*c* show the device and the views from FIGS. 2*a*, 2*b* and 2*c*, respectively, where the needle shielding sleeve is in its needle shielding position.

After the injection has taken place, the needle shielding sleeve 3 can be moved relative to the housing 2 from the actuated position along the longitudinal axis L by a needle shielding stroke $H_N$ in the distal direction into a needle shielding position (FIGS. 7a-7c). In the needle shielding position, the distal end of the needle shielding sleeve 3 protrudes distally beyond the needle tip of the injection needle 13a, so that access to the needle tip is prevented and a risk of injury is reduced. As will be described further below, the needle shielding sleeve 3 can be blocked against pushing back out again from the needle shielding position.

The multichamber syringe holder 1 has a projection 1a which points radially outward, where the projection 1a engages in a slot-shaped recess of the needle shielding sleeve 3, which is arranged between the housing 2 and the multichamber syringe holder 1. In the initial position of the needle shielding sleeve 3 (FIGS. 2a-2c) and/or in the needle shielding position of the needle shielding sleeve 3 (FIGS. 7a-7c), the needle shielding sleeve 3, such as the proximal end of the slot-shaped recess, may rest against the projection 1a, whereby a movement of the needle shielding sleeve 3 in the distal direction is prevented. A cam 1b, which may be arranged resiliently on the multichamber syringe holder 1 and is formed by the multichamber syringe holder 1, can engage in this slot-shaped recess, or alternatively in another recess of the needle shielding sleeve 3. The cam 1b may be configured such that, in the attempt to move the needle shielding sleeve 3 from the initial position into the actuated position, the cam 1b initially prevents the movement of the needle shielding sleeve 3, where the cam 1b is pressed out when the force applied to the needle shielding sleeve 3 to push it back exceeds a certain threshold value, where the needle shielding sleeve 3 is abruptly pushed back into the actuated position. The injection needle 13a may thereby be inserted into the puncture site. In order to insert the injection needle 13a or to move the needle shielding sleeve 3 into the actuated position, the distal end of the needle shielding sleeve 3 may be placed into the puncture site, where the housing 2 may then be pressed in the direction of the puncture site, where when the pressing force exceeds the aforementioned threshold value, the housing 2 may be abruptly moved toward the puncture site and the needle shielding sleeve 3 may be moved relative to the housing 2 into the actuated position.

The housing 2 may have a cylindrical holding portion or cylinder portion 2b. The holding portion of the housing may surround the snap-in hook 4a of the pull-off cap 4 in the delivery state of the autoinjector. The holding portion of the housing 2 may serve to prevent a movement of the snap-in hook 4a transversely to the longitudinal axis from the longitudinal axis. In the case of a movement of the pull-off cap 4 in the distal direction, it can thus be ensured that the catch 4b of the pull-off cap 4 remains in engagement with the needle shielding cap 14 of the multichamber syringe 13. Furthermore, the housing 2 in the region of the holding portion 2b can have a translation stop in the form of a holding shoulder 2e (FIG. 2b), which may prevent the multichamber syringe holder 1 from being movable relative to the housing 2 in the distal direction when the multichamber syringe holder 1 rests against the holding shoulder 2e. Furthermore, the cylindrical holding portion 2b may include grooves 2d which, in conjunction with rails 3c, which are attached to the inside of the needle shielding sleeve 3, may form an anti-rotation lock for the needle shielding sleeve 3.

The autoinjector may further include a sleeve-shaped drive element 7, which may forms ribs 7c (FIG. 3c) projecting inward and in the longitudinal direction at its distal end, against which ribs 7c a first spring 9—which can also be referred to as discharge spring—braces. The first spring 9 may be arranged within the sleeve-shaped drive element 7. The length of the ribs 7c may be configured in such a way that the installation space for the first spring 9, which is a helical spring acting as a compression spring, is reduced and thus the spring 9 is biased in the initial or delivery state of the autoinjector with a sufficient amount of energy that it can discharge the product contained in the multichamber syringe 13, such as completely by moving the drive element 7 by a discharge stroke $H_A$ (FIG. 2c), from the second chamber 13f and the first chamber 13e of the multichamber syringe 13. In addition, the ribs 7c may form a reinforcement of the base of the drive element 7, so that the distal region of the drive element 7 does not fracture due to the high forces of the discharge spring 9. In the delivery state of the device, there is a distance between the first plunger 13b and the distal end of the drive element 7, so that the drive element 7 only hits the first plunger 13b during the execution of the discharge stroke $H_A$ and entrains the latter in the discharge direction.

The first spring 9 braces at its proximal end against a holding element 6, which in this example, has two arms 6c, where a first engagement element 6a and a second engagement element 6b is arranged on each arm 6c. The first engagement element 6a points radially toward the longitudinal axis L, where the second engagement element 6b points radially away from the longitudinal axis L. The first engagement element 6a engages in a first recess 7a, which is formed by the drive element 7, thereby preventing movement of the drive element 7 relative to the holding element 6 in the distal direction or in the discharge direction. As a result, the first spring 9 is held in its tensioned state. The holding element 6 may include a guide pin 6d which is inserted through the proximal end of the first spring 9 into the core of the spring 9. The guide pin 6d may prevent a lateral buckling of the first spring 9 during and at the end of the discharge stroke $H_A$ of the drive element 7.

The autoinjector has a switching module 8, 15 which has a switching sleeve 15 and a locking sleeve 8 surrounded by the switching sleeve 15. In the initial or delivery state of the device, the first engagement element 6a is held in engagement with the first recess 7a by the inner circumference of the locking sleeve 8, which rests against the second engagement element 6b.

The switching sleeve 15 is connected to the proximal end 3a of the needle shielding sleeve 3 or at least rests against the proximal end 3a of the needle shielding sleeve 3. A second spring 10, which can also be referred to as a needle shielding spring, within which the first spring 9 is arranged and which at least partially surrounds the switching sleeve 15 and the locking sleeve 8, braces with its distal end against the switching sleeve 15. A part of the switching sleeve 15 may thus be arranged between the needle shielding sleeve 3 and the distal end of the second spring 10. The second spring 10 may be a spring made of metal which acts as a compression spring and may be configured as a helical spring. The proximal end of the second spring 10 may brace against a signal member 11, such as against a projection 11*c*, which engages in an axially movable and rotationally fixed manner in the housing 2 and which extends through a slot-shaped groove 5*b* of the mechanism holder 5. The second spring 10 may thus also surround the mechanism holder 5 at least partially or completely.

The switching sleeve 15 has one or more recesses 15*a*, in which a corresponding locking member 8*a* of the locking sleeve 8 engages. The locking member 8*a* may be sawtooth-shaped and project radially away from the longitudinal axis L. The locking member 8*a* may be resiliently arranged on an arm which may be formed by the locking sleeve 8. By moving the switching sleeve 15 in the proximal direction, the locking sleeve 8 may be entrained in the proximal direction by the engagement of the locking member 8*a*.

By moving the needle shielding sleeve 3 into the actuated position, the switching sleeve 15 may also be entrained by the actuation stroke $H_B$, thereby tensioning the second spring 10. If the needle shielding sleeve 3 is not moved completely into the actuated position, the second spring 10 can move the switching sleeve 15 and the needle shielding sleeve 3 back into the initial position, where the locking sleeve 8 is also entrained by the switching sleeve 15 via the engagement of the locking member 8*a*.

In the delivery state or before the triggering of the discharge of the product, the sleeve-shaped signal member 11 may be in an axially fixed engagement with the drive element 7. The signal member 11 has a first engagement member 11*a*, which may engage in a recess 7*b* of the drive element 7, and a second engagement member 11*b*. The first engagement member 11*a* and the second engagement member 11*b* may be resiliently arranged on the end of an arm 11*d*. The signal member 11 may include two such arms 11*d* with a first engagement member 11*a* and a second engagement member 11*b*. The first engagement member 11*a* may point radially toward the longitudinal axis L, whereas the second engagement member 11*b* may point radially away from the longitudinal axis L. In the delivery state, the first engagement member 11*a* may be held by the inner circumference of the locking sleeve 8 in an axially fixed engagement with the drive element 7. In alternative embodiments, the recess 7*b*, for instance a recess 7*b* extending in the longitudinal direction, may be configured in such a way that, during a first partial stroke of the discharge stroke, an axial relative movement may take place between the drive element 7 and the signal member 11 and, during a second partial stroke of the discharge stroke, the first engagement member 11*a* may be held in an axially fixed engagement, at least in the distal direction, with the drive element 7. The second engagement member 11*b* may rest against the inner circumference of the switching sleeve 8. The closure cap 12 may include a signal stop 12*b*, which the signal member 11 can hit against for generating a signal and against which the signal member 11 rests in the delivery state of the device.

Figures 3A, 3B, 3C:
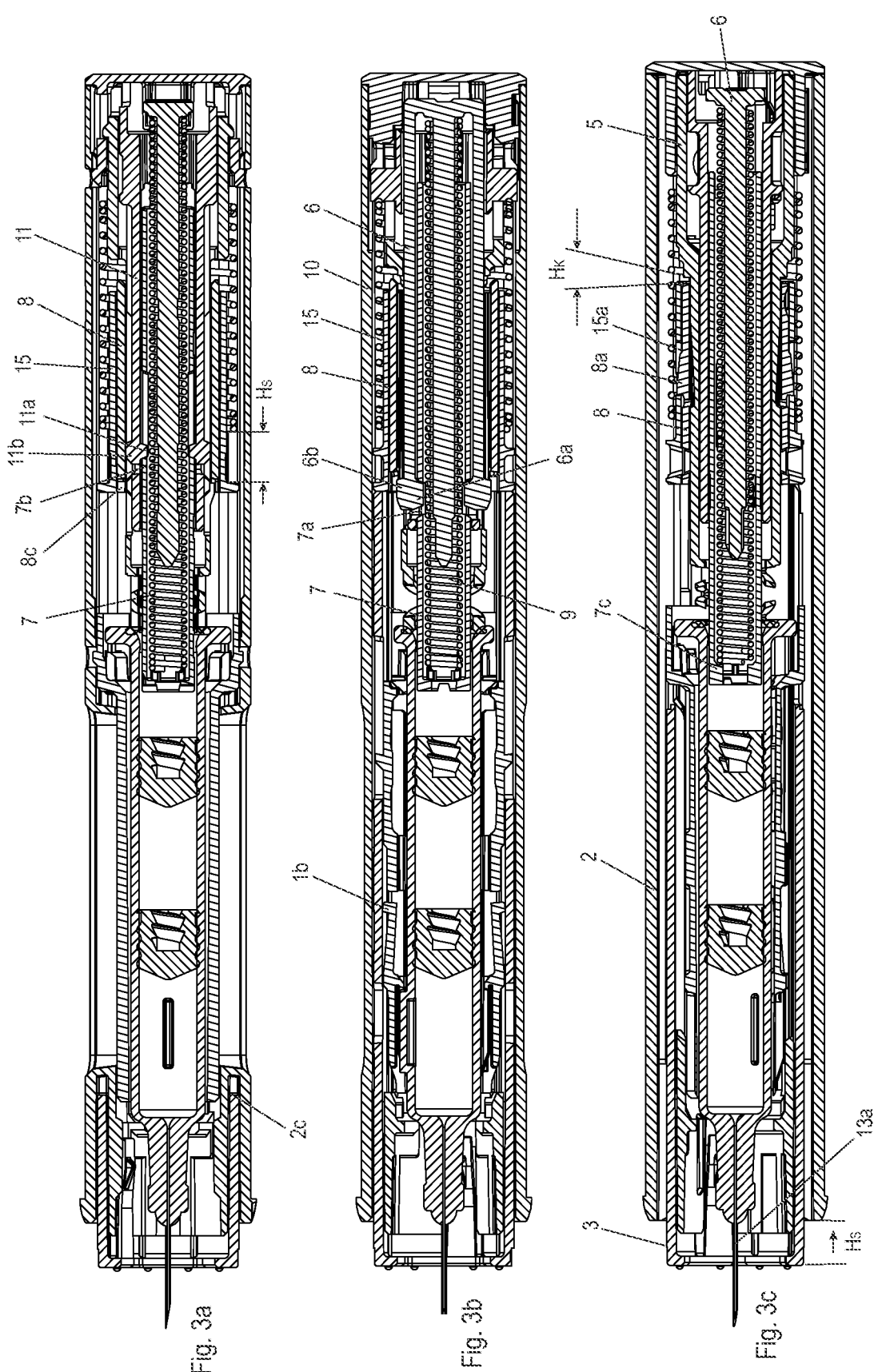
FIGS. 3*a*, 3*b* and 3*c* show the device and the views from FIGS. 2*a*, 2*b*, and 2*c*, respectively, where a needle shielding sleeve is in its actuated position.

To administer the product from the multichamber syringe 13, the pull-off cap 4 may be removed from the autoinjector together with the rigid needle shield 14. The distal end of the needle shielding sleeve 3 may be placed at the puncture site of a patient, where the housing 2 may be moved toward the puncture site, and where the needle shielding sleeve 3 moves from its initial position into the actuated position by the actuation stroke $H_B$ in the proximal direction relative to the housing 2. As a result, the second spring 10 is tensioned, where the switching sleeve 15 is entrained by the needle shielding sleeve 3 by the actuation stroke $H_B$. The locking sleeve 8 has a first recess 8*b*, which is brought to the position of the second engagement element 6*b* along the longitudinal axis L by moving the locking sleeve 8 by the actuation stroke $H_B$, as shown in FIGS. 3*a*-3*c*. As a result, the first engagement element 6*a* is moved out of engagement with the drive element 7 with a movement transverse to and away from the longitudinal axis L, where at the same time the second engagement element 6*b* is moved into engagement with the locking sleeve 8, the first recess 8*b* thereof. As a result, the drive element 7 is enabled for the movement by the discharge stroke $H_A$ in the discharge direction.

Because the axially fixed coupling between the drive element 7 and the holding element 6 is now released, the holding element 6, which can be moved at least to a certain extent relative to the housing 2 and along the longitudinal axis L, can be moved by the first spring 9 in the proximal direction, where the holding element 6 entrains the locking sleeve 8 by a start signal stroke $H_K$ (FIG. 3*c*) by engaging the second engagement element 6*b* in the recess 8*b*, whereby the locking sleeve 8 hits against a start signal stop 5*a*, which is formed by the mechanism holder 5, and thereby outputs an acoustic and/or tactile signal which signals to the user of the device that the discharge of the product has started. As a result of the movement of the locking sleeve 8 by the actuation stroke $H_B$, the locking member 8*a* is enabled for a movement transversely and toward the longitudinal axis L because the mechanism holder 5 has a depression 5*d*, which allows such a movement of the locking member 8*a* when the locking sleeve 8 has been moved by the actuation stroke $H_B$ or when the needle shielding sleeve 3 is in its actuated position.

Figures 4A, 4B, 4C:
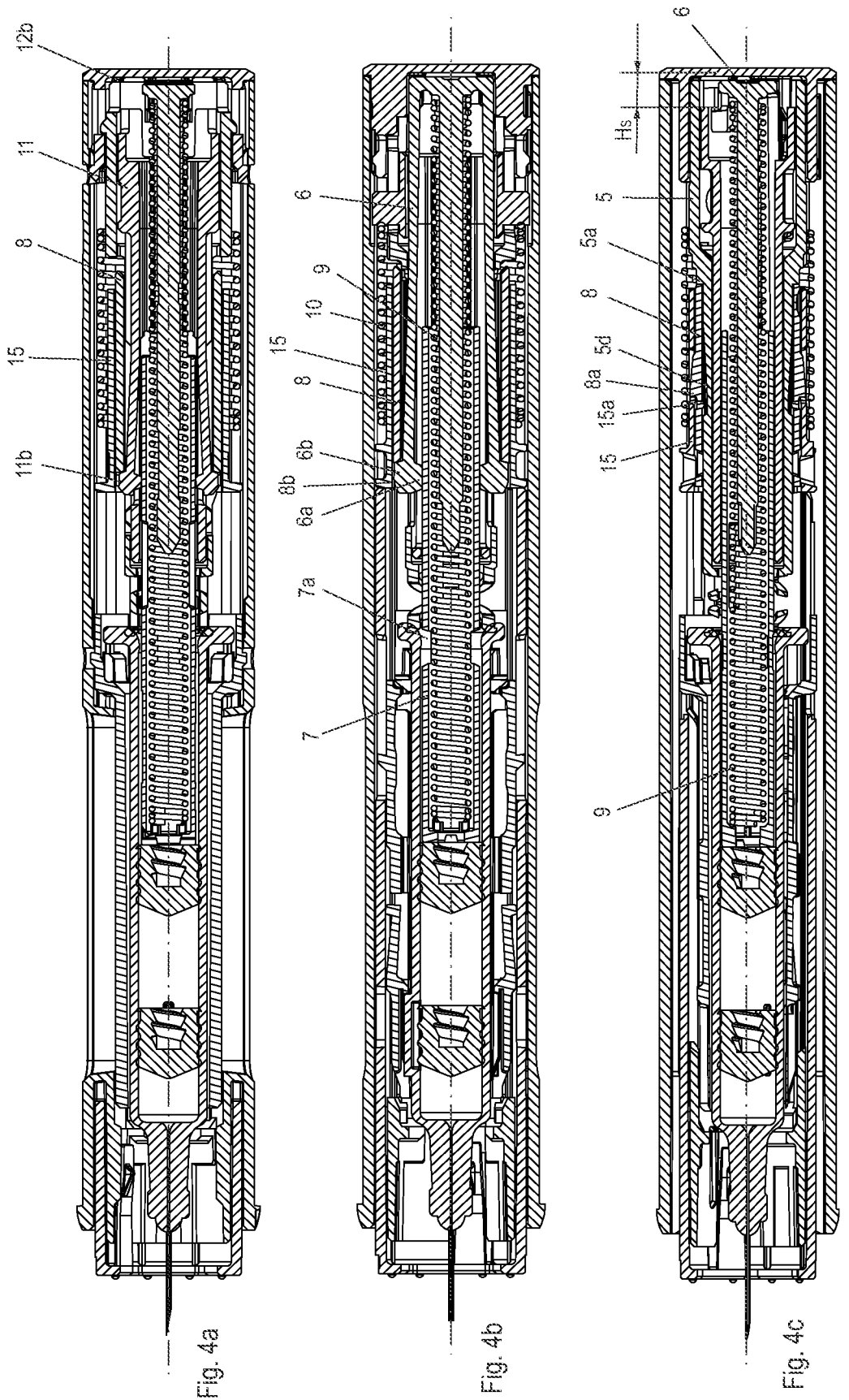
FIGS. 4*a*, 4*b* and 4*c* show the device and the views from FIGS. 2*a*, 2*b*, and 2*c*, respectively, where a drive element is shown at the end of a first partial stroke of its discharge stroke.

Because the signal member 11 is still connected in an axially fixed manner to the drive element 7, it is entrained by a first partial stroke $H_S$ of the discharge stroke $H_A$ in the discharge direction, where the signal member 11 is moved away from the signal stop 12*b*, approximately by the first partial stroke $H_S$, as can best be seen from FIG. 4*c*. At the end of the first partial stroke $H_S$, during which the first and second engagement members 11*a*, 11*b* are moved relative to the locking sleeve 8, the first engagement member 11*a* is pressed out of engagement with the drive element 7, where at the same time the second engagement member 11*b* is moved into the second recess 8*c* of the locking sleeve 8 with a movement transverse to the longitudinal axis L and radially away from the longitudinal axis L. As a result, the signal member 11 is prevented from moving in the proximal direction relative to the housing 2 or the locking sleeve 8. The second engagement member 11*b* is held in engagement with the recess 8*c* by the outer circumference of the drive element 7 (FIG. 4*a*) when the drive element 7 is moved by its second partial stroke of the discharge stroke $H_A$. The outer circumferential surface of the drive element 7 holds the second engagement element 6*b* in engagement with the first recess 8*b* of the locking sleeve 8, as can best be seen from FIG. 4*b*. At the end of the discharge stroke $H_A$, the drive element 7 releases the second engagement member 11*b* from the engagement with the locking sleeve 8, where the second engagement member 11*b* is moved out of engagement with the recess 8*c*, toward the longitudinal axis L, so that the second spring 10 accelerates the signal member 11 counter to the discharge direction, e.g., in the proximal direction, so that an acoustic and/or tactile signal is generated when the signal member 11 strikes the signal stop 12*b*.

Figures 5A, 5B, 5C:
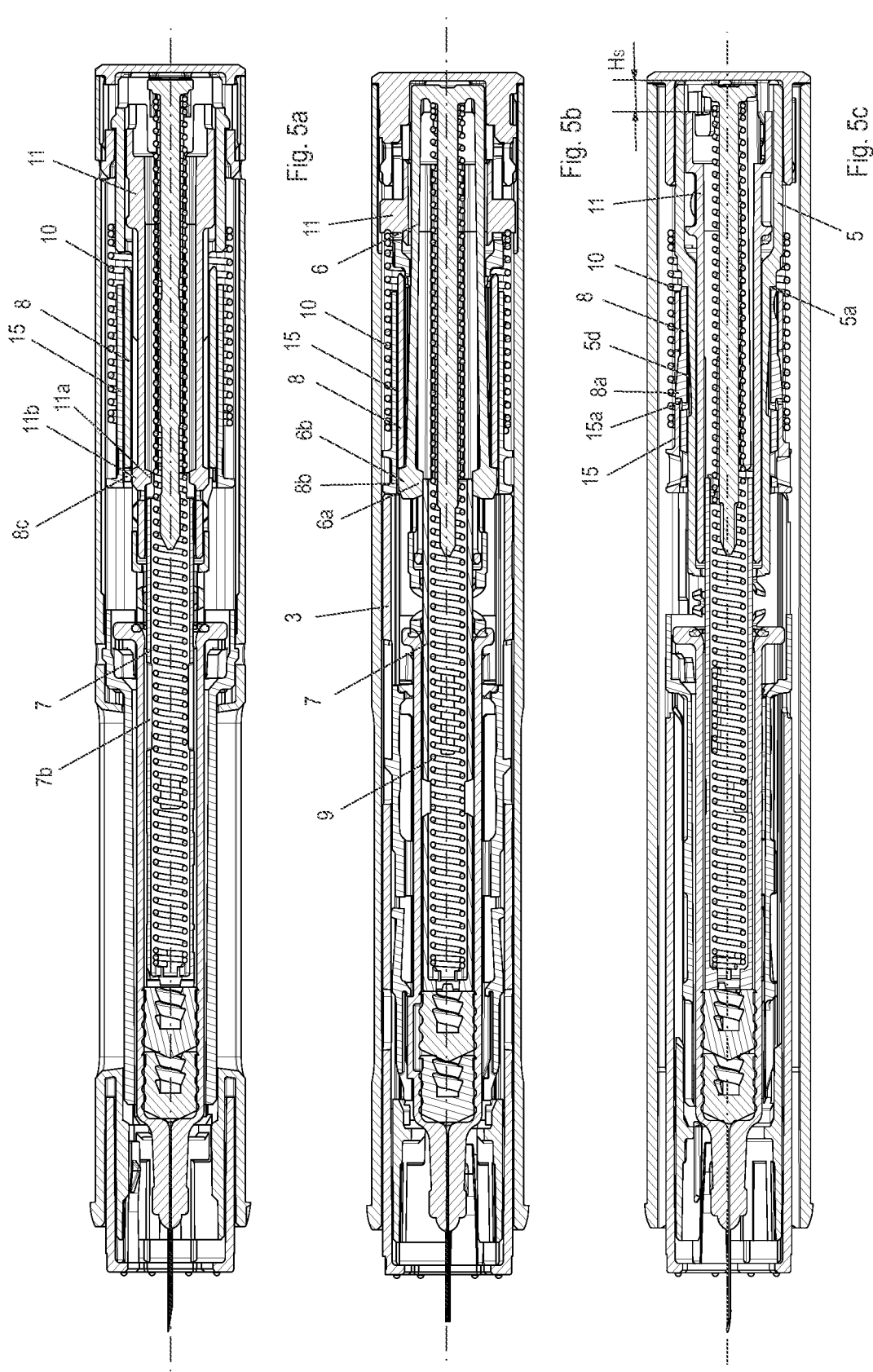
FIGS. 5*a*, 5*b*, and 5*c* show the device and the views from FIGS. 2*a*, 2*b*, and 2*c*, respectively, where the drive element is shown at the end of its discharge stroke.
Figures 6A, 6B, 6C:
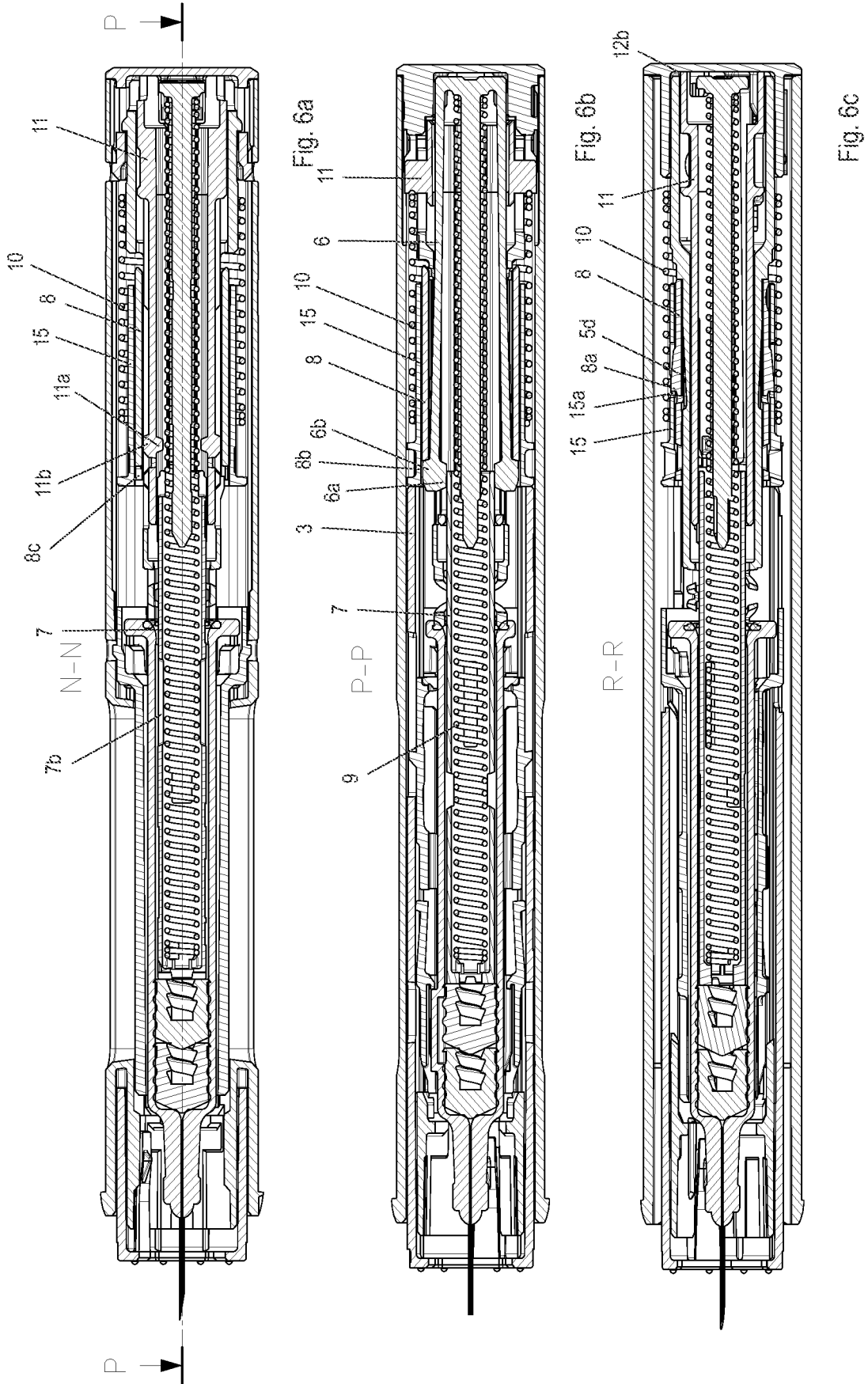
FIGS. 6*a*, 6*b* and 6*c* show the device and the views from FIGS. 2*a*, 2*b* and 2*c*, respectively, where a signal is generated which signals the end of the discharge of the product.

As can best be seen from FIG. 5*b*, the engagement of the second engagement element 6*b* in the first recess 8*b* remains, where a movement of the locking sleeve 8 in the distal direction relative to the housing 2 is prevented.

By removing the autoinjector from the injection site, the second spring 10 can move the switching sleeve 15 and the needle shielding sleeve 3 from the actuated position into the needle shielding position by the needle shielding stroke H$_N$, where the locking member 8a is pressed out of engagement with the recess 15a, where the switching sleeve 15 moves relative to the locking sleeve 8 in the distal direction. When the needle shielding sleeve 3 is in its needle shielding position, the locking member 8a snap-fits with the switching sleeve 15, where the locking member 8a prevents the needle shielding sleeve 3 from being pushed back into its actuated position. In the attempt to push the needle shielding sleeve 3 back from the needle shielding position into the actuated position, the switching sleeve 15 hits against the locking member 8a, which may prevent the movement of the needle shielding sleeve 3 into the actuated position. For this purpose, the locking sleeve 8 may brace axially against the start signal stop 5a of the mechanism holder 5.

| List of reference signs | |
| --- | --- |
| 1 | Multichamber syringe holder |
| 1a | Projection/holding element |
| 1b | Cam |
| 1c | Cutout |
| 1d | Distal stop |
| 1e | Proximal stop |
| 2 | Housing |
| 2a | Recess |
| 2b | Cylindrical holding portion |
| 2c | Stop/actuation stop |
| 2e | Holding shoulder |
| 2d | Grooves |
| 3 | Needle shielding sleeve |
| 3a | Proximal end |
| 3b | Snap geometry |
| 3c | Rails |
| 4 | Pull-off cap |
| 4a | Snap-in hook |
| 4b | Catch |
| 5 | Mechanical holder |
| 5a | Start signal stop |
| 5b | Groove |
| 5c | Retaining spring portion |
| 5d | Indentation |
| 6 | Holding element |
| 6a | First engagement element |
| 6b | Second engagement element |
| 6c | Arm |
| 6d | Guide pin |
| 7 | Drive element |
| 7a | First recess |
| 7b | Second recess |
| 7c | Ribs |
| 8 | Locking sleeve |
| 8a | Locking element |
| 8b | First recess |
| 8c | Second recess |
| 9 | First spring/discharge spring |
| 10 | Second spring/needle shielding spring |
| 11 | Signal member |
| 11a | First engagement member |
| 11b | Second engagement member |
| 11c | Protrusion |
| 11d | Arm |
| 12 | Closure cap |
| 12a | Latching member |
| 12b | Signal stop |
| 13 | Multichamber syringe |
| 13a | Injection needle |
| 13b | First plunger |
| 13b' | Second plunger |
| 13c | Syringe body |
| 13d | Bypass |

-continued

| List of reference signs | |
| --- | --- |
| 13e | First chamber |
| 13f | Second chamber |
| 13g | Finger flange |
| 14 | Rigid needle shield/needle shielding cap |
| 15 | Switching sleeve |
| 15a | Recess |
| H$_A$ | Discharge stroke |
| H$_B$ | Actuation stroke |
| H$_S$ | Signal stroke/first partial stroke |
| H$_K$ | Start signal stroke |
| H$_N$ | Needle shielding stroke |
| H$_M$ | Installation stroke |
| L | Longitudinal axis |

What is claimed is:

1. An autoinjector for discharging one or more liquid products, comprising:
a housing;
a multichamber product container arranged in the housing and comprising a syringe body and an injection needle rigidly coupled to a distal end of the syringe body, wherein the syringe body comprises a first chamber configured for a first liquid product, a second chamber configured for a second liquid product, and a bypass for fluidically connecting the first chamber and second chamber, wherein the bypass is formed in or on the syringe body as a curved section protruding radially outward, wherein a first plunger and a second plunger are arranged in the syringe body in an axially movable manner, wherein the first liquid product and the second liquid product in an initial position of the autoinjector are separated from one another by the second plunger, and wherein the first plunger and/or the second plunger are movable in a discharge direction in order to discharge the product contained in the multichamber product container or the plurality of products contained in the multichamber product container;
a drive element configured to act on the first plunger during a discharge of the product; and
a first spring configured to act on the drive element, wherein a bias of first spring is sufficient such that the first spring is configured to discharge the liquid product or the plurality of liquid products out of the second chamber of the multichamber product container by moving the drive element by a discharge stroke; and
a multichamber product container holder fixedly arranged in the housing,
wherein the housing or the multichamber product container holder comprises a cutout within which the bypass is received, the cutout configured with a distal stop and a proximal stop that axially fix the bypass such that the multichamber product container is axially fixed in the housing or in the multichamber product container holder.

2. The autoinjector according to claim 1, wherein in the cutout is configured to taper to rotationally fix the bypass.

3. The autoinjector according to claim 1, wherein the cutout is formed in an elastically and/or plastically deformable manner.

4. The autoinjector according to claim 1, wherein one or more of the cutout, the proximal stop, and the distal stop are formed in an elastically and/or plastically deformable manner.

5. The autoinjector according to claim 1, wherein the cutout comprises the distal stop, and wherein a force acting on the multichamber product container in a distal direction holds the multichamber product container against the distal stop when the multichamber product container is inserted in the housing or in the multichamber product container holder.

6. The autoinjector according to claim 5, wherein one or more of the cutout and the distal stop are formed in an elastically and/or plastically deformable manner.

\* \* \* \* \*